US009101534B2

(12) United States Patent
Bochenko

(10) Patent No.: US 9,101,534 B2
(45) **Date of Patent: *Aug. 11, 2015**

(54) MEDICATION AND IDENTIFICATION INFORMATION TRANSFER APPARATUS

(75) Inventor: Walter John Bochenko, Encinitas, CA (US)

(73) Assignee: CRISI Medical Systems, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/282,255

(22) Filed: Oct. 26, 2011

(65) Prior Publication Data

US 2012/0037266 A1 Feb. 16, 2012

Related U.S. Application Data

(63) Continuation-in-part of application No. 12/768,509, filed on Apr. 27, 2010.

(51) Int. Cl.
*A61J 1/20* (2006.01)
*A61B 19/00* (2006.01)

(52) U.S. Cl.
CPC .......... *A61J 1/2096* (2013.01); *A61J 2001/201* (2013.01); *A61J 2205/10* (2013.01); *A61J 2205/20* (2013.01); *A61J 2205/30* (2013.01); *A61J 2205/60* (2013.01)

(58) Field of Classification Search
CPC ..................... A61J 2001/2065; A61J 2205/00; A61J 2205/30; A61J 2205/20; A61J 2205/10; A61J 2205/60
USPC ................. 604/403–407, 411–416; 141/1, 98
See application file for complete search history.

(56) References Cited

U.S. PATENT DOCUMENTS

| | | | |
|---|---|---|---|
| 4,650,475 | A | 3/1987 | Smith et al. |
| 4,853,521 | A | 8/1989 | Claeys et al. |

(Continued)

FOREIGN PATENT DOCUMENTS

| | | | |
|---|---|---|---|
| DE | 29617777 | U1 | 12/1996 |
| EP | 1980974 | A2 | 10/2008 |

OTHER PUBLICATIONS

International Search Report dated Aug. 2, 2011 for corresponding PCT Application No. PCT/US2010/055322.

(Continued)

*Primary Examiner* — Loan H Thanh
*Assistant Examiner* — Andrew S Lo
(74) *Attorney, Agent, or Firm* — The Webb Law Firm

(57) ABSTRACT

A medication and identification information transfer system is provided that includes a primary medication container, a secondary medication container, a secondary container label and a medication information transfer apparatus. The medication information transfer apparatus, when coupled to the primary medication container, can transfer information indicative of the contents of the primary medication container to a medication delivery device such as an intelligent injection site. The medication information transfer apparatus has a shape and size enabling it to be connected to an adapter for removal of medication from the primary medication container which enables transfer of the medication to a secondary container while simultaneously transferring information about the medication in the primary medication container to the injection site. In some implementations, the medication injection site can be placed on a fluid delivery line for infusion into a patient. Related apparatus, systems, methods and kits are also disclosed.

19 Claims, 22 Drawing Sheets

(56) References Cited

U.S. PATENT DOCUMENTS

| | | | |
|---|---|---|---|
| 4,978,335 | A | 12/1990 | Arthur, III |
| 5,279,576 | A | 1/1994 | Loo et al. |
| 5,338,157 | A | 8/1994 | Blomquist |
| 5,628,309 | A | 5/1997 | Brown |
| 5,651,775 | A | 7/1997 | Walker et al. |
| 5,692,640 | A | 12/1997 | Caulfield et al. |
| 5,713,856 | A | 2/1998 | Eggers et al. |
| 5,781,442 | A | 7/1998 | Engleson et al. |
| 5,782,814 | A | 7/1998 | Brown et al. |
| 5,792,117 | A | 8/1998 | Brown |
| 5,833,213 | A | 11/1998 | Ryan |
| 5,873,731 | A | 2/1999 | Prendergast |
| 5,920,263 | A | 7/1999 | Huttenhoff et al. |
| 5,941,846 | A | 8/1999 | Duffy et al. |
| 5,984,901 | A | 11/1999 | Sudo et al. |
| 6,019,745 | A | 2/2000 | Gray |
| 6,039,251 | A | 3/2000 | Holowko et al. |
| 6,123,686 | A | 9/2000 | Olsen et al. |
| 6,270,455 | B1 | 8/2001 | Brown |
| 6,277,099 | B1 | 8/2001 | Strowe et al. |
| 6,338,200 | B1 | 1/2002 | Baxa et al. |
| 6,471,089 | B2 | 10/2002 | Liff et al. |
| 6,497,680 | B1 | 12/2002 | Holst et al. |
| 6,519,569 | B1 | 2/2003 | White et al. |
| 6,579,231 | B1 | 6/2003 | Phipps |
| RE38,189 | E | 7/2003 | Walker et al. |
| D481,121 | S | 10/2003 | Evans |
| 6,671,563 | B1 | 12/2003 | Engelson et al. |
| D485,356 | S | 1/2004 | Evans |
| 6,685,678 | B2 | 2/2004 | Evans et al. |
| 6,731,989 | B2 | 5/2004 | Engleson et al. |
| 6,790,198 | B1 | 9/2004 | White et al. |
| 6,851,615 | B2 | 2/2005 | Jones |
| 6,915,170 | B2 | 7/2005 | Engleson et al. |
| 6,960,192 | B1 | 11/2005 | Flaherty et al. |
| 6,993,402 | B2 | 1/2006 | Klass et al. |
| 7,061,831 | B2 | 6/2006 | De La Huerga |
| 7,074,205 | B1 | 7/2006 | Duffy et al. |
| 7,074,209 | B2 | 7/2006 | Evans et al. |
| 7,096,072 | B2 | 8/2006 | Engleson et al. |
| 7,103,419 | B2 | 9/2006 | Engleson et al. |
| 7,107,106 | B2 | 9/2006 | Engleson et al. |
| 7,115,113 | B2 | 10/2006 | Evans et al. |
| 7,117,041 | B2 | 10/2006 | Engleson et al. |
| 7,161,488 | B2 | 1/2007 | Frasch |
| 7,171,277 | B2 | 1/2007 | Engleson et al. |
| 7,364,067 | B2 | 4/2008 | Steusloff et al. |
| 7,370,797 | B1 | 5/2008 | Sullivan et al. |
| 7,384,410 | B2 | 6/2008 | Eggers et al. |
| 7,470,266 | B2 | 12/2008 | Massengale et al. |
| 7,483,756 | B2 | 1/2009 | Engleson et al. |
| 7,722,083 | B2 | 5/2010 | McCarthy et al. |
| 7,727,196 | B2 | 6/2010 | Neer |
| 7,771,385 | B2 | 8/2010 | Eggers et al. |
| 7,813,939 | B2 | 10/2010 | Clements et al. |
| 7,834,816 | B2 | 11/2010 | Marino et al. |
| 7,922,073 | B2 | 4/2011 | de la Huerga |
| 7,933,780 | B2 | 4/2011 | De La Huerga |
| 7,991,627 | B2 | 8/2011 | Hutchinson et al. |
| 8,035,517 | B2 | 10/2011 | Gibson |
| 8,151,835 | B2 | 4/2012 | Khan et al. |
| 8,240,550 | B2 | 8/2012 | Steusloff et al. |
| 8,303,547 | B2 | 11/2012 | Brown |
| 8,480,834 | B2 | 7/2013 | Rice et al. |
| 8,505,809 | B2 | 8/2013 | Steusloff et al. |
| 8,636,202 | B2 | 1/2014 | Keefe et al. |
| 8,639,521 | B2 | 1/2014 | Eggers et al. |
| 8,639,525 | B2 | 1/2014 | Levine et al. |
| 8,645,154 | B2 | 2/2014 | Eggers et al. |
| 2001/0056258 | A1* | 12/2001 | Evans ........................... 604/131 |
| 2002/0040208 | A1 | 4/2002 | Flaherty et al. |
| 2002/0077852 | A1 | 6/2002 | Ford et al. |
| 2002/0098598 | A1 | 7/2002 | Coffen et al. |
| 2002/0099334 | A1 | 7/2002 | Hanson et al. |
| 2002/0188259 | A1 | 12/2002 | Hickle et al. |
| 2003/0012701 | A1 | 1/2003 | Sangha et al. |
| 2003/0052787 | A1 | 3/2003 | Zerhusen et al. |
| 2003/0055685 | A1 | 3/2003 | Cobb et al. |
| 2003/0065537 | A1 | 4/2003 | Evans |
| 2003/0088238 | A1 | 5/2003 | Poulsen et al. |
| 2003/0135388 | A1 | 7/2003 | Martucci et al. |
| 2003/0139701 | A1 | 7/2003 | White et al. |
| 2003/0140929 | A1 | 7/2003 | Wilkes et al. |
| 2003/0174326 | A1 | 9/2003 | Rzasa et al. |
| 2004/0051368 | A1 | 3/2004 | Caputo et al. |
| 2004/0082918 | A1 | 4/2004 | Evans et al. |
| 2004/0186437 | A1 | 9/2004 | Frenette et al. |
| 2004/0204673 | A1 | 10/2004 | Flaherty |
| 2005/0101905 | A1 | 5/2005 | Merry |
| 2005/0106225 | A1 | 5/2005 | Massengale et al. |
| 2005/0182358 | A1 | 8/2005 | Veit et al. |
| 2005/0277890 | A1 | 12/2005 | Stewart et al. |
| 2006/0079767 | A1 | 4/2006 | Gibbs et al. |
| 2006/0079843 | A1 | 4/2006 | Brooks et al. |
| 2006/0116639 | A1 | 6/2006 | Russell |
| 2006/0122577 | A1 | 6/2006 | Poulsen et al. |
| 2006/0144942 | A1 | 7/2006 | Evans et al. |
| 2006/0190302 | A1 | 8/2006 | Eggers et al. |
| 2006/0226089 | A1 | 10/2006 | Robinson et al. |
| 2006/0229551 | A1 | 10/2006 | Martinez et al. |
| 2006/0253346 | A1 | 11/2006 | Gomez |
| 2006/0258985 | A1 | 11/2006 | Russell |
| 2006/0287887 | A1 | 12/2006 | Hutchinson et al. |
| 2007/0043335 | A1 | 2/2007 | Olsen et al. |
| 2007/0136218 | A1 | 6/2007 | Bauer et al. |
| 2007/0166198 | A1 | 7/2007 | Sangha et al. |
| 2007/0167919 | A1 | 7/2007 | Nemoto et al. |
| 2007/0186923 | A1 | 8/2007 | Poutiatine et al. |
| 2007/0191787 | A1 | 8/2007 | Lim et al. |
| 2007/0279625 | A1 | 12/2007 | Rzasa et al. |
| 2007/0299421 | A1 | 12/2007 | Gibson |
| 2008/0045930 | A1 | 2/2008 | Makin et al. |
| 2008/0051937 | A1 | 2/2008 | Khan et al. |
| 2008/0061153 | A1 | 3/2008 | Hickle et al. |
| 2008/0125724 | A1 | 5/2008 | Monroe |
| 2008/0191013 | A1 | 8/2008 | Liberatore |
| 2008/0208042 | A1 | 8/2008 | Ortenzi et al. |
| 2008/0234630 | A1 | 9/2008 | Iddan et al. |
| 2008/0243088 | A1 | 10/2008 | Evans |
| 2008/0294108 | A1 | 11/2008 | Briones et al. |
| 2009/0018494 | A1 | 1/2009 | Nemoto et al. |
| 2009/0036846 | A1 | 2/2009 | Dacquay et al. |
| 2009/0043253 | A1 | 2/2009 | Podaima |
| 2009/0069714 | A1 | 3/2009 | Eichmann et al. |
| 2009/0069743 | A1 | 3/2009 | Krishnamoorthy et al. |
| 2009/0113996 | A1 | 5/2009 | Wang et al. |
| 2009/0126483 | A1 | 5/2009 | Blendinger et al. |
| 2009/0149744 | A1 | 6/2009 | Nemoto et al. |
| 2009/0157008 | A1 | 6/2009 | Vitral |
| 2009/0159654 | A1 | 6/2009 | Grimard |
| 2009/0209911 | A1 | 8/2009 | Cabus et al. |
| 2009/0294521 | A1 | 12/2009 | de la Huerga |
| 2010/0065643 | A1 | 3/2010 | Leyvraz et al. |
| 2010/0152562 | A1 | 6/2010 | Goodnow et al. |
| 2010/0153136 | A1 | 6/2010 | Whittacre et al. |
| 2010/0174266 | A1 | 7/2010 | Estes |
| 2010/0179417 | A1 | 7/2010 | Russo |
| 2010/0262002 | A1 | 10/2010 | Martz |
| 2010/0280486 | A1 | 11/2010 | Khair et al. |
| 2010/0305499 | A1 | 12/2010 | Matsiev et al. |
| 2011/0060198 | A1 | 3/2011 | Bennett et al. |
| 2011/0111794 | A1 | 5/2011 | Bochenko et al. |
| 2011/0112473 | A1 | 5/2011 | Bochenko et al. |
| 2011/0112474 | A1 | 5/2011 | Bochenko et al. |
| 2011/0152824 | A1 | 6/2011 | DiPerna et al. |
| 2011/0160655 | A1 | 6/2011 | Hanson et al. |
| 2011/0220713 | A1 | 9/2011 | Cloninger |
| 2011/0224649 | A1 | 9/2011 | Duane et al. |
| 2011/0264069 | A1 | 10/2011 | Bochenko |
| 2011/0313349 | A1 | 12/2011 | Krulevitch et al. |
| 2012/0004542 | A1 | 1/2012 | Nemoto et al. |
| 2012/0037266 | A1 | 2/2012 | Bochenko |
| 2012/0041355 | A1 | 2/2012 | Edman et al. |
| 2012/0222468 | A1 | 9/2012 | Nelson et al. |

(56) References Cited

U.S. PATENT DOCUMENTS

| | | | |
|---|---|---|---|
| 2012/0226446 | A1 | 9/2012 | Nelson et al. |
| 2012/0226447 | A1 | 9/2012 | Nelson et al. |
| 2013/0105568 | A1 | 5/2013 | Jablonski et al. |
| 2013/0181046 | A1 | 7/2013 | Fedorko et al. |
| 2013/0226137 | A1 | 8/2013 | Brown |
| 2013/0327822 | A1 | 12/2013 | Keefe et al. |
| 2014/0039383 | A1 | 2/2014 | Dobbles et al. |
| 2014/0060729 | A1 | 3/2014 | Srnka et al. |
| 2014/0142975 | A1 | 5/2014 | Keefe et al. |
| 2015/0011976 | A1 | 1/2015 | Vouillamoz et al. |

OTHER PUBLICATIONS

Google Scholar Search [Jul. 21, 2014].

* cited by examiner

MEDICATION AND IDENTIFICATION INFORMATION TRANSFER APPARATUS

RELATED APPLICATIONS

This application is a continuation-in-part of U.S. patent application Ser. No. 12/768,509 filed on Apr. 27, 2010 entitled: "Medication and Identification Information Transfer Apparatus", the contents of which are hereby fully incorporated by reference.

FIELD

The subject matter described herein relates to a medication and identification information transfer apparatus for use with identifying the contents of medication containers such as syringes, vials, cartridges, and medication bags and bottles.

BACKGROUND

Many health care procedures involve a sequence of medication administrations to complete a specialized protocol. The type of medication and timing of administration are important to record in order to provide healthcare providers real-time information on the conduct of the procedure and the completion of a medical record. Some specialized protocols require quick medication administrations with limited time for documentation and record keeping. As an important part of safe drug preparation of medications into secondary containers healthcare providers should include labeling to reduce errors as recommended by The Joint Commission accreditation program. Pharmaceutical manufacturers produce many types of primary medication containers and include prefilled syringes, prefilled cartridges, vials, ampoules, bottles and bags. The transfer and proper identification of medications from primary containers to secondary containers can be challenging.

SUMMARY

Medications are provided in primary containers by pharmaceutical manufacturers and take many forms like vials, ampoules, prefilled syringes, prefilled cartridges, bottles, bags and custom containers. Frequently these primary containers require fluid access and medication transfer to secondary containers like syringes, admixture bags/bottles and IV administration tubing sets to enable the delivery of medications to a patient. The secondary containers can then couple to fluid delivery channels such as "Y" sites on IV tubing sets or extension sets, multi-port manifolds and catheters for administration to patients. At each step in the medication transfer process it is important to clearly identify and document what and how much medication is transferred. The medication and identification information transfer apparatus provides both human and machine readable information about the various medication transfer activity and enables improved labeling and documentation of the events. There are any number of various primary and secondary container types used for the delivery of medications to patients and various transfer methods used. The specific devices, methods, and sequences can be varied. Only a few are described in detail in this application.

In one aspect, a medication and information transfer apparatus is provided that includes an information transfer element, an information element affixed to, deposited to, or forming an integral part of the information transfer element and a primary-to-secondary container adapter (e.g. vial adapter). The information transfer element includes a fluid inlet fitting and a fluid outlet fitting. The information transfer element can fluidically couple to a primary-to-secondary container adapter (e.g. vial adapter) at the fluid outlet. The information transfer element can fluidically couple to a secondary container (e.g. an empty syringe) at the fluid inlet. The information element is disposed on the information transfer element and contains information indicative of the contents of a primary medication container (prefilled syringe, prefilled cartridge, vial, ampoule, bottle, bag). The information element can contain human and/or machine readable information.

The shape and size of the information transfer element can be such that it can mate with the housing of a medication injection site (that in turn can determine the contents of the medication vial/container using the information transfer element). The shape and size of the vial adapter can be such that it provides access to large and small medication vials and/or ampuoles. The vial adapter can be a conventional needle, a blunt tip cannula, a clip-on adapter with spike and vial clips, or a needleless access port with spike among many other possible configurations. However, in some embodiments, the size of the vial adapter female luer fitting is only one size.

The information transfer element fluid inlet can be a female luer fitting having a surface that engages the male luer fitting tip of a secondary container (syringe, bag, bottle, IV tubing set) and will retain the information transfer element when the secondary container (e.g. syringe) is removed from the vial adapter. In other embodiments, the information transfer element can include a luer lock fitting in addition to the male luer fitting. In this case, the internal and/or external surface of the syringe luer lock hub can engage and retain the information transfer element when the syringe is removed from the vial adapter. The secondary container (empty syringe, etc.) can be used to withdraw medication from a primary container (vial, etc.) containing medication for transfer to an injection site. The information transfer element fluid outlet is a male luer fitting having a surface that can disengage from the female luer fitting of the vial adapter.

The syringe can be a suitable size that is equal to or greater than the volume of medication to be withdrawn from the vial. The vial can contain a single dose volume of medication or a multiple dose volume of medication. The information on the information transfer element can contain the appropriate single dose volume.

A removable sterility cap can be affixed to the information transfer element fluid inlet for the protection of sterility. The spike of the vial adapter can contain a removable sterility cap for protection of sterility. When used these sterility caps are removed, but can be replaced as required. Alternatively, the information transfer element fluid inlet can be a needleless access port allowing multiple syringes to be used for multiple withdrawals from a multi-dose vial. Alternatively, the vial adapter female luer fitting can be a needleless access port allowing multiple connections of the information transfer element to be used for multiple withdrawals from a multi-dose vial.

The medication information transfer apparatus can be enveloped in a sterile pouch (i.e., enclosure, tube, rigid or semi-rigid etc.) or other suitable sterile packaging. The sterile pouch can contain information indicative of the information on the information transfer element. The medication and identification information transfer apparatus can be part of a kit that also contains the primary container (prefilled syringe, prefilled cartridge, vial, ampoule, bottle, bag), a secondary label and/or medication instructions for use. The kit can be manufactured complete by a pharmaceutical company including the medication in the vial and the information transfer apparatus. The kit can be packaged by a local pharmacy or contract pharmacy services company and can include a pharmaceutical company packaged primary container, a secondary label and the information transfer apparatus. In the pharmacy kit configuration the pharmacy can match and verify the medication information on the vial and vial packaging with the medication information on the information transfer apparatus packaging and the information transfer element. Once matched and verified the pharmacy can join the vial and information transfer apparatus into a package and label the kit. The package can provide a tamper evident element providing assurance of maintaining the matched elements. Alternatively, the information transfer apparatus can be provided in a sterile package with an empty side pouch for insertion of a primary container after identification verification. A tamper evident seal can be closed and marked with a pharmacy label to indicate completed verifications.

The identification element can be machine readable disposed radially about a central fluid outlet axis of the fluid outlet tip enabling detection of the information when the medication container is rotated about the central fluid outlet axis. The identification element can be a ring shaped member configured to fit around the fluid outlet tip of the information transfer element. The identification element can include human readable information to indicate the medication information.

The information can be selected from a group comprising: optically encoded information, magnetically encoded information, radio frequency detectable information, capacitively and/or inductively detectable information, mechanically detectable information, human readable information. The human readable information can be both right-side up and up-side down to allow user readability during the inverted medication transfer from the vial to a syringe and during attachment to an IV administration injection site when the user's hand or fingers may be holding the syringe barrel and limiting view of the medication information. The human readable information can include a selection of any of a medication name, concentration, expiration time/date, medication classification color, a unique identifier.

In one aspect, a system can include a medication vial, a secondary medication container, and an information transfer apparatus. The medication vial contains medication. The secondary medication container receives or extracts the medication contained within the medication vial when the secondary medication container is in fluid communication with the medication vial. The information transfer apparatus is configured to couple to the medication vial to the secondary medication container such that, subsequent to the secondary medication container being in fluid communication with the medication vial, at least a portion of the information transfer apparatus physically transfers and remains affixed to the secondary medication container. In addition, the information transfer apparatus includes an information element to enable characterization of the medication.

In another aspect, a system includes a medication vial, a secondary medication container, and an information transfer apparatus. Unlike implementations in which the information transfer apparatus is first coupled to the medication vial, in this arrangement, the information transfer element remains coupled to the secondary medication container. With such variations, the information transfer apparatus can include an information transfer element, a vial adapter configured to couple to the information transfer element on a first end and to pierce and/or couple to the medication vial on a second end, and an information element characterizing medicine contained within the medication vial. In this variation the secondary medication container (syringe) can include the information transfer element. The information transfer element can be included as part of the syringe, added to the syringe as a mark or label, pre-attached and separable, or otherwise joined with the syringe.

In yet another variation, there can be two secondary containers and two medication transfers. The primary medication container can be a vial and the first secondary container can be a syringe. Medication and identification information transfer can be completed from the vial to the first secondary container (syringe). Subsequently, the vial adapter can be removed from the vial and next inserted in to a second secondary container (an IV bag). The secondary container bag can already contain fluid (a medication, sterile water, D5W, saline, ringers lactate, etc.). The medication and identification information can be transferred a second time into the second secondary container (bag) for administration to a patient. The information transfer element can be coupled to IV administration tubing at the distal end for final coupling to an administration fluid channel connected to a patient. The IV tubing with information transfer element can be coupled to an intelligent IV site for information transfer to a data collection system.

Various combinations of the primary medication container, the secondary medication container, secondary label and the information transfer apparatus can be packaged together to form a portion of a kit. The packaging can be shrink wrap, a sterile pouch, a sterile tube or other plastic enclosure or it can be a cardboard or paper box. Additionally, within or on the packaging instructions can be provided to ensure that one or more of the medication vial, the secondary medication container, and the information transfer apparatus include the correct or matching identifiers. Additionally, within or on the packaging a second drug specific secondary label can be provided to allow the user to clearly mark and identify the contents of the secondary medication container after medication is transferred from the vial. This secondary label can contain the drug name, concentration, classification color, expiration date, drug NDC code, drug NDC barcode, unique identifier, or other information indicative of the medication to be transferred. This secondary label can also provide space for user notations to indicate one or more of preparer's name, preparation date, expiration date, indication of dilution, indication of mixing, storage instructions (protect from light, refrigerate, etc.), patient ID/name, medication administration instructions. The secondary label can contain machine readable information (optical, barcode, magnetic, RFID) to allow the user to read information for automated data transfer.

Some healthcare providers can mix two medications together prior to administration to a patient. In these situations packaging can include two primary medication containers (vials, etc.). The information transfer apparatus is used twice (once for each of two primary medication containers) and can contain labeling to indicate a "mix" of two medications.

In a further interrelated aspect, an information transfer apparatus can be coupled to a secondary medication container. Thereafter, a primary medication container containing medication is coupled to the information transfer apparatus while it is coupled to the secondary medication container to enable fluid communication between the primary medication container and the secondary medication container. The information transfer apparatus can have an information element to enable characterization of the medication. Subsequently, medication is extracted from the primary medication container using the secondary medication container. The secondary medication container is then decoupled from the primary medication container. The information transfer apparatus is configured such that, during the decoupling, at least a portion of the information transfer apparatus automatically affixes or remains affixed to the secondary medication container. Medication within the secondary medication container can be later administered via a medication delivery device (e.g., intelligent injection site, etc.) that can read the information element affixed to the secondary medication container to characterize the medication.

In still a further interrelated aspect, an information transfer apparatus is coupled to a first secondary medication container. An information transfer apparatus is then coupled to a primary medication container containing medication while it is coupled to the first secondary medication container to enable fluid communication between the primary medication container and the first secondary medication container. The information transfer apparatus includes an information element to enable characterization of the first medication. The first medication is then extracted from the primary medication container using the first secondary medication container. Thereafter, the first secondary medication container is decoupled from the primary medication container. The information transfer apparatus is then coupled to a second secondary container while it is coupled to the first secondary medication container to enable fluid communication between the first secondary container and the second secondary container. The first medication within the first secondary medication container is later delivered into the second secondary medication container which has a fluid delivery outlet. Next, the information transfer apparatus is decoupled from the second secondary medication container. At least a portion of the information transfer apparatus is, at this time, affixed to the fluid delivery outlet of the second secondary medication container so that the information element can be read by a medication delivery device to characterize the first medication.

In yet a further interrelated aspect, an information transfer apparatus is coupled to a secondary medication container. The information transfer apparatus is then coupled to a first primary medication container while it is coupled to the secondary medication container to enable fluid communication between the first primary medication container and the secondary medication container. The information transfer apparatus having an information element to enable characterization of a first primary medication and a second primary medication. Thereafter, first medication is extracted from the first primary medication container using the secondary medication container. The information transfer apparatus is then decoupled from the first primary medication container while it remains coupled to the secondary medication container. The information transfer apparatus is later coupled to a second primary medication container while it is coupled to the secondary medication container to enable fluid communication between the second primary medication container and the secondary medication container. Second medication is then extracted from the second primary medication container using the secondary medication container to result in mixed medications. The secondary medication container is later decoupled from the second primary medication container. The information transfer apparatus is configured such that, during the decoupling, at least a portion of the information transfer apparatus automatically affixes or remains affixed to the secondary medication container. Administration of the mixed medication within the medication container is then enable via a medication delivery device. The medication delivery device can read the information element affixed to the secondary medication container characterizing the mixed medications.

The details of one or more variations of the subject matter described herein are set forth in the accompanying drawings and the description below. Other features and advantages of the subject matter described herein will be apparent from the description and drawings, and from the claims.

DESCRIPTION OF THE DRAWINGS

The accompanying drawings, which are incorporated in and constitute a part of this specification, show certain aspects of the subject matter disclosed herein and, together with the description, help explain some of the principles associated with the disclosed embodiments. In the drawings.

Like reference symbols in the various drawings indicate like or similar elements.

DETAILED DESCRIPTION

Figure 1:
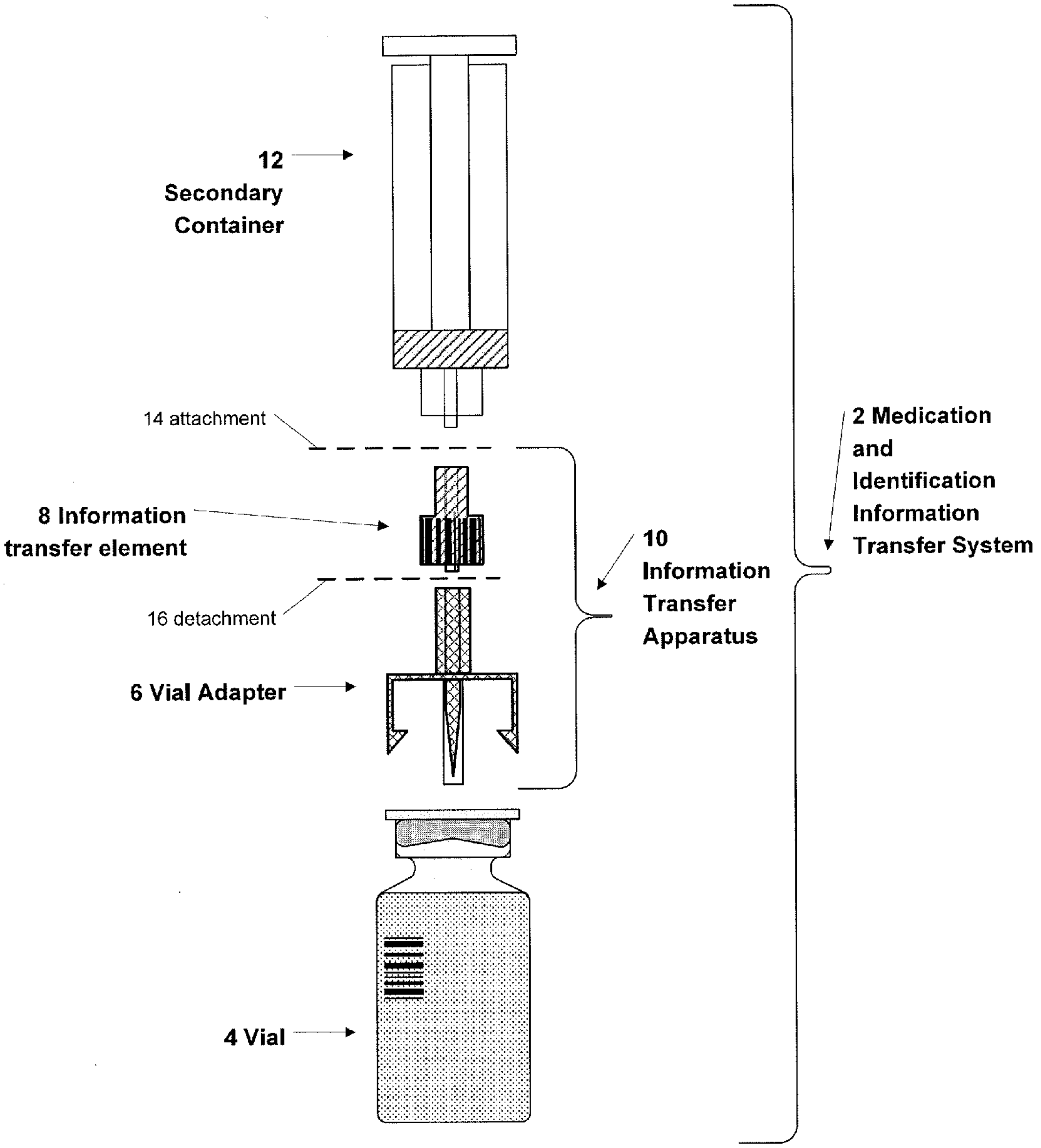
FIG.1 is a diagram illustrating a medication and identification information transfer system.

FIG. 1 is a diagram illustrating a medication and identification information transfer system 2 in which a healthcare provider can access medication from primary container (vial 4) for transfer and administration to a patient. In particular, the healthcare provider can select vial 4 from an array of available vials and transfer the medication and medication information to a patient's medication delivery device. The medication delivery devices can automatically detect the contents of a medication container being used to administer medication to a patient. Examples of medication delivery devices include medication injection sites and related data collection systems as described in U.S. patent application Ser. Nos. 12/614,276, 12/765,707 and 12/938,300 all entitled "Medication Injection Site and Data Collection System", the contents of each of these applications are hereby fully incorporated by reference.

Vial adapter 6 and information transfer element 8 can be joined to form information transfer apparatus 10. Information transfer apparatus 10 can be used to puncture vial 4 to access the medication for transfer to secondary container 12 (a syringe). Syringe 12 can initially be provided empty and can be attached 14 to information transfer apparatus 10 for the purpose of withdrawing medication from vial 4. The healthcare provider withdraws medication from vial 4 into syringe 12 and detaches (16) syringe 12 from vial 4 carrying with it information transfer element 8 which can contain information indicative of the medication withdrawn from vial 4. Syringe 12 and the medication contents are now identified for transfer to a patient for injection. A health care provider can inject the medication in syringe 12 by first attaching or otherwise coupling information transfer element 8 to an intelligent medication injection site (such as those described and illustrated in U.S. patent application Ser. Nos. 12/614,276, 12/765,707 and 12/938,300 all entitled "Medication Injection Site and Data Collection System"), at time of attachment to the injection site medication information contained on information transfer element 8 (described later) can be identified by the injection site (or other device) so that the medication injected into the patient can be identified and/or logged. In one implementation, a medication injection site can comprise: a housing; a fluid conduit at least partially extending within the first housing and configured to deliver medication within a medication container to the patient; a medication port extending from an external surface of the first housing configured to be coupled to a fluid outlet of the medication container, the medication port being fluidically and directly coupled to the fluid conduit; the at least one sensor, wherein the at least one sensor is disposed within the housing to generate data characterizing administration of the medication; a transmitter within the housing to wirelessly transmit data generated by the sensor to a remote data collection system; and a self-contained power source within the housing powering the at least one sensor and the transmitter.

Figure 2:
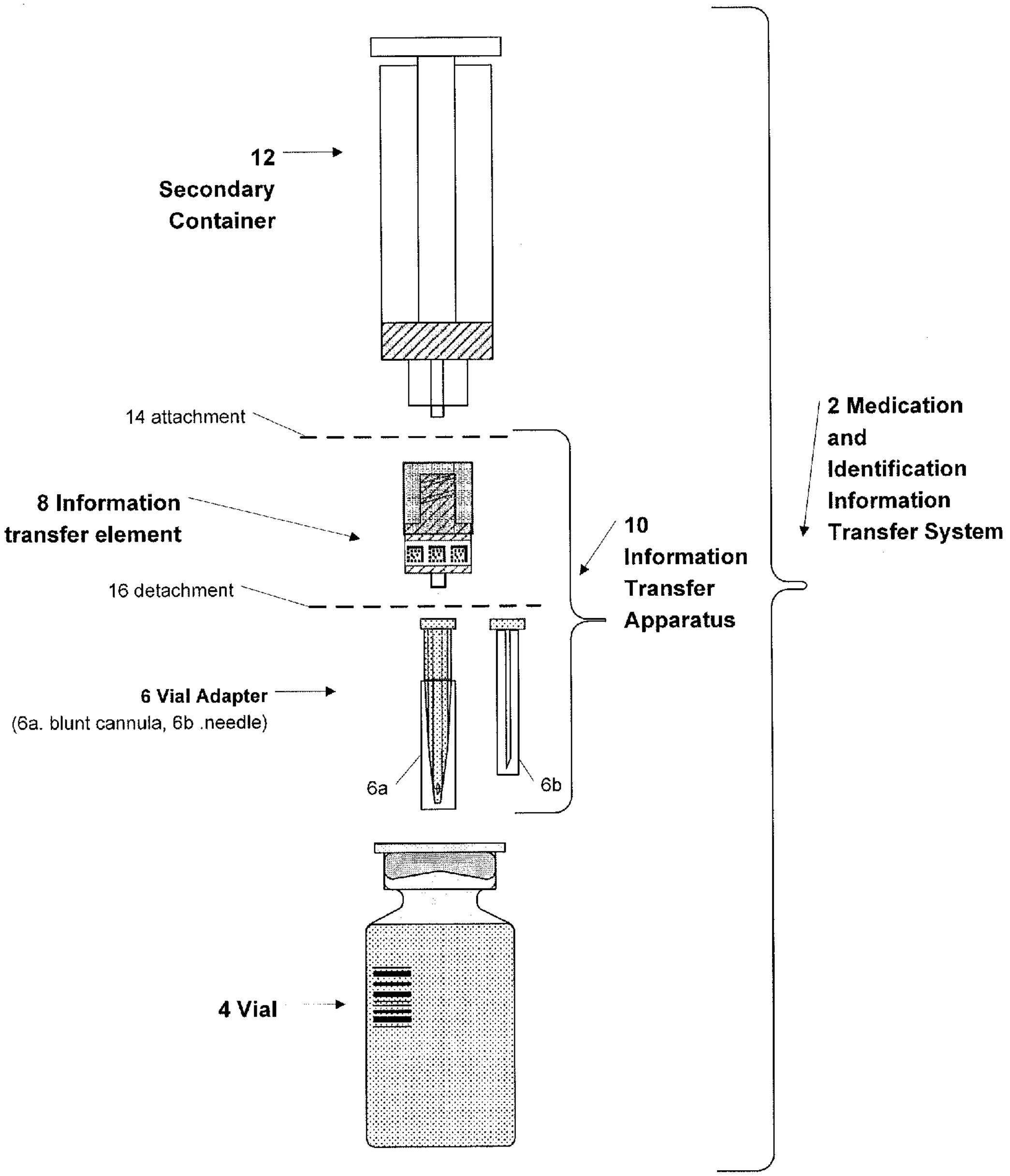
FIG.2 is a diagram illustrating an alternate medication and identification information transfer system.

FIG. 2 is a diagram illustrating an alternate medication and identification information transfer system 2 in which a healthcare provider can access medication from vial 4 for transfer and administration to a patient. In this variation, vial adapter 6 can be a blunt tip cannula 6*a* or needle 6*b* and information transfer element 8 can be joined to form information transfer apparatus 10. Similar to FIG. 1, information transfer apparatus 10 can be used to puncture vial 4 to access the medication for transfer to secondary container 12 (a syringe). Syringe 12 can initially be provided empty and can be attached 14 to information transfer apparatus 10 for the purpose of withdrawing medication from vial 4. The healthcare provider withdraws medication from vial 4 into syringe 12 and detaches (16) syringe 12 from vial 4 carrying with it information transfer element 8 which can contain information indicative of the medication withdrawn from vial 4. Syringe 12 and the medication contents are now identified for transfer to a patient for injection.

Figure 3:
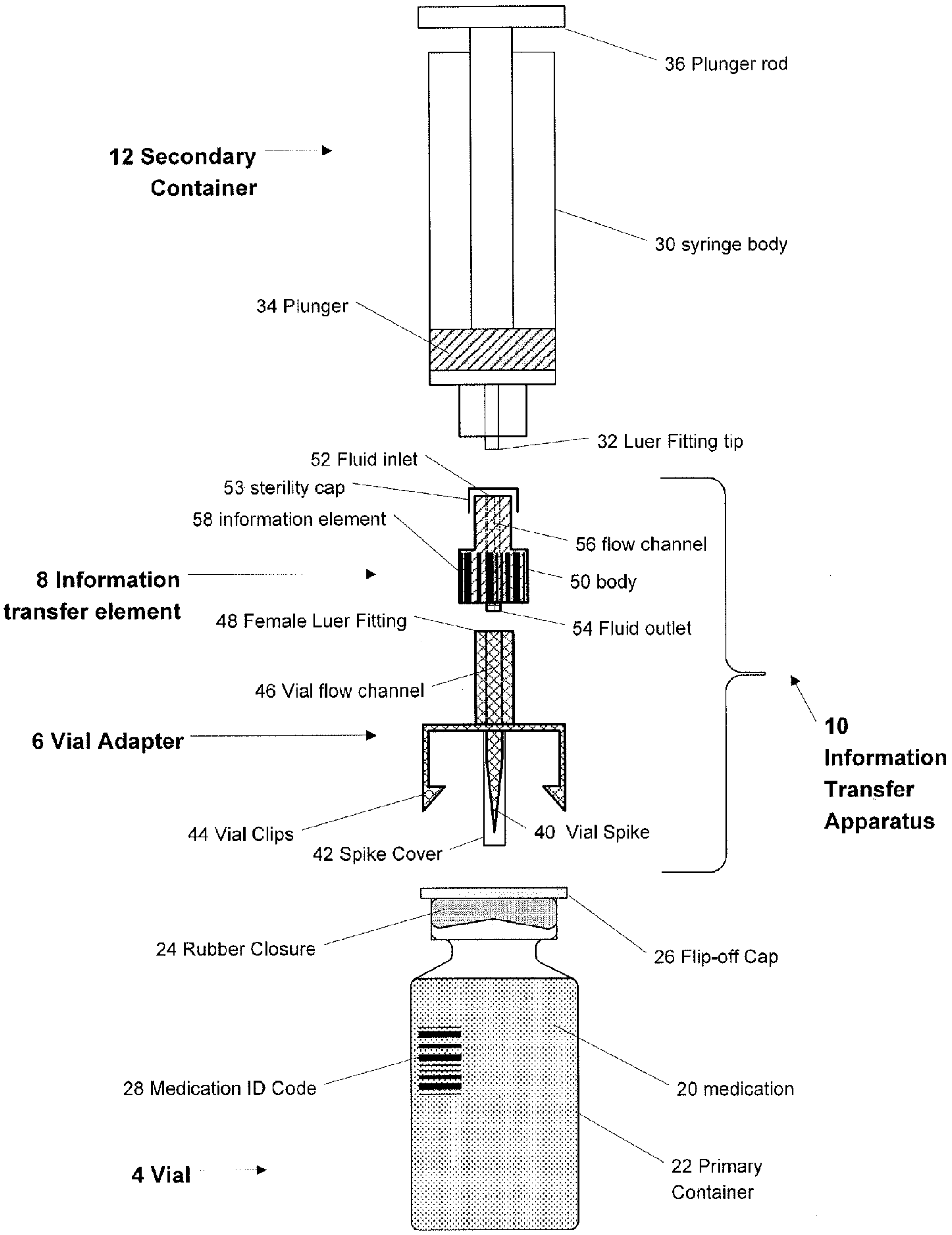
FIG. 3 is a diagram describing a detailed view of a medication and identification information transfer system as in FIG. 1.

FIG. 3 is a diagram describing a detailed view of a medication and identification information transfer system 2 as in FIG. 1. At the bottom of the figure, medication vial 4 contains medication 20 within primary container 22. At the top of vial 4 the open end of primary container 22 can be closed by rubber closure 24 and protected by flip off cap 26. Vial 4 can carry an information source 28 (e.g., medication ID code, NDC number, etc.) that provides detectable information indicative of the medication contents in primary container 22 and/or of the volume of the contents. Vial 4 as used herein refers to prefilled syringes, prefilled cartridges, vials, ampoules and other primary medication containers such as bags and bottles (except when explicitly disclaimed). It can be appreciated that many configurations of vial 4 can be manufactured and can function in system 2.

At the top of the figure, secondary container 12 can be a syringe with syringe body 30, male luer fitting tip 32, plunger 34 and plunger rod 36. Secondary container 12 as used herein refers to syringes and other secondary medication containers such as admixture bags or bottles, IV tubing sets, etc. (except when explicitly disclaimed). It can be appreciated that many configurations of secondary container 12 can be manufactured and can function in system 2.

In the center of FIG. 3 information transfer apparatus 10 can comprise vial adapter 6 joined with information transfer element 8. Vial adapter 6 can be a sterilizable plastic material and can comprise vial spike 40 with spike cover 42, vial clips 44, vial flow channel 46 and a female luer fitting 48. It can be appreciated that many configurations of vial adapter 6 can be manufactured and can function in system 2 (provided that the vial adapter can create a sterile fluid pathway between the vial 4, information transfer element 8 and the secondary medication container 12).

Information transfer element 8 can be a sterilizable injection molded plastic material comprising element body 50, fluid inlet 52, fluid inlet sterility cap 53, fluid outlet 54, flow channel 56 and information element 58.

Information element 58 can be one or more of an optical source, a magnetic source, a mechanical source, a switchable RFID source, a conductive source, and/or a proximity source. One implementation can provide information encoded within information element 58 in the form of an optically detectable surface, reflective or absorbing light, that is embedded into or on top of element body 50. Information element 58 can include both machine readable information and human readable information.

Alternatively, information provided by information element 58 can be a magnetically detectable strip similar to a credit card magnetic strip, facilitating a magnetic scan similar to credit card swiping, that is embedded into or on top of element body 50.

Further and alternatively, information provided by information element 58 can be a mechanically detectable feature comprising Braille like features of bumps or ridges or valleys on the surface of or at the end of element body 50, facilitating mechanical detection by one or more microswitchs or similar physical detection method such as a lock-and-key mechanism.

Further and alternatively, information provided by information element 58 can be an RFID tag located on the surface of element body 50, facilitating detection by an RFID reader. The antenna of the RFID tag can be switchable and would be OPEN prior to connection to a medication injection site. Upon connection to the medication injection site the antenna can become CLOSED (or connected) facilitating RFID reader detection. When the transfer apparatus 10 is disconnected from the medication injection site the RFID tag antenna can again become OPEN.

Further and alternatively, information provided by information element 58 can be in the form of a capacitive or inductive proximity feature on the surface of or embedded into element body 50, facilitating capacitive or inductive proximity detection.

The information element 58 can be an integrated feature of the information transfer element 8 such as etched or molded features. The information element 58 can alternatively be adhered or deposited to element body 50 (i.e., information element 58 can be a label, etc.) or embedded therein. In addition, the information element 58 can be a separate element that extends around fluid outlet 54.

When information transfer apparatus 10 is manufactured, vial adapter 6 can be joined with information transfer element 8 by attaching fluid outlet 54 to female luer fitting 48. This assembly can be packaged, sterilized and provided together with vial 4 or provided separately (see FIG. 5). Alternate packaging configurations will be described later.

Figure 4:
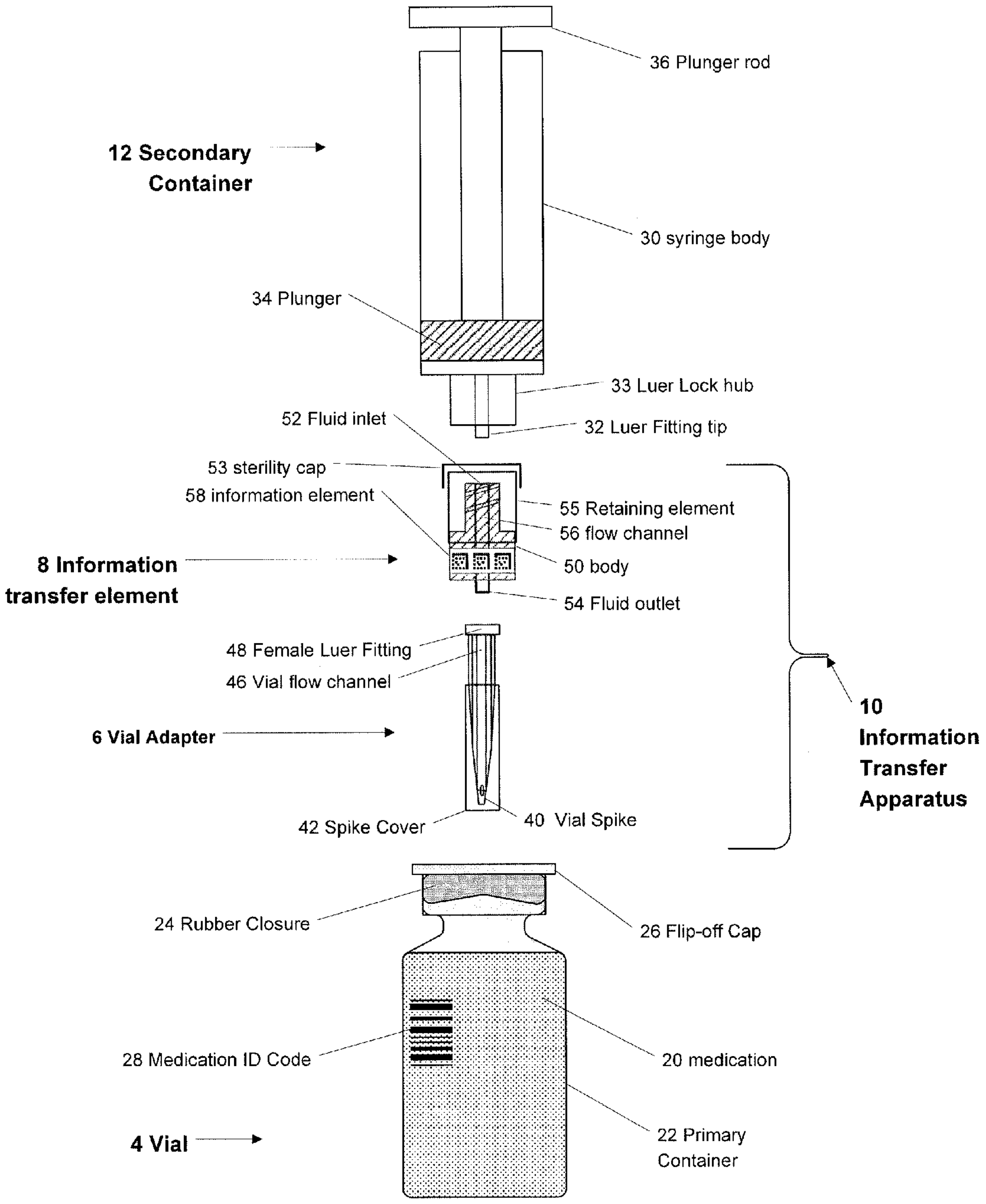
FIG. 4 is a diagram describing a detailed view of an alternate medication and identification information transfer system as in FIG. 2.

FIG. 4 is a diagram describing a detailed view of an alternate medication and identification information transfer system as in FIG. 2. Similar to FIG. 3, in this variation, at the bottom of the figure, medication vial 4 contains medication 20 within primary container 22. At the top of the figure, secondary container 12 can be a syringe with syringe body 30, male luer fitting tip 32, plunger 34 and plunger rod 36. The syringe tip can contain a luer lock hub 33. In the center information transfer apparatus 10 comprises vial adapter 6 (shown with blunt tip cannula **6*a*) joined with information transfer element 8. Vial adapter 6 can be a sterilizable plastic or metal material and comprises vial spike or hypodermic needle 40 with spike or needle cover 42, vial flow channel 46 and a female luer fitting 48. It can be appreciated that many configurations of vial adapter 6 can be manufactured and can function in system 2 provided that the vial adapter can create a sterile fluid pathway between the vial 4, information transfer element 8 and the secondary medication container 12**.

A key aspect of the current subject matter is information transfer element 8 which can be a sterilizable injection molded plastic material comprising element body 50, fluid inlet 52, sterility cap 53, fluid outlet 54, flow channel 56, retaining element 55 and information element 58.

Retaining element 55 can be a semi-stretchable material like silicone rubber or plasticized PVC allowing initial stretching and positive gripping of the outer surface of syringe luer lock hub 33. Retaining element 55 can be straight or formed with an enlarged and tapered proximal end to easily accept luer lock hub 33 when inserted. When fully inserted luer lock hub 33 engages with the stretched retaining element 55 forming a positive grip engagement. At the other distal end of information transfer element 8, female luer fitting 48 connects vial flow channel 46 to fluid outlet 54 forming a releasable engagement as shown later in FIG. 8. Retaining element 55 can alternatively be a mechanical snap action coupling, an adhesive coupling, a threaded coupling, a splined coupling, and lock-and-key type coupling or other method of positively securing secondary container 12 to information transfer element 8.

Similar to FIG. 3, information element 58 can be one or more of an optical source (example: two dimensional barcode matrix), a magnetic source, a mechanical source, a switchable RFID source, a conductive source, and/or a proximity source. One implementation can provide information encoded within information element 58 in the form of an optically detectable surface, reflective or absorbing light, that is embedded into or on top of element body 50. Information element 58 can include both machine readable information and human readable information.

Figures 5, 6:
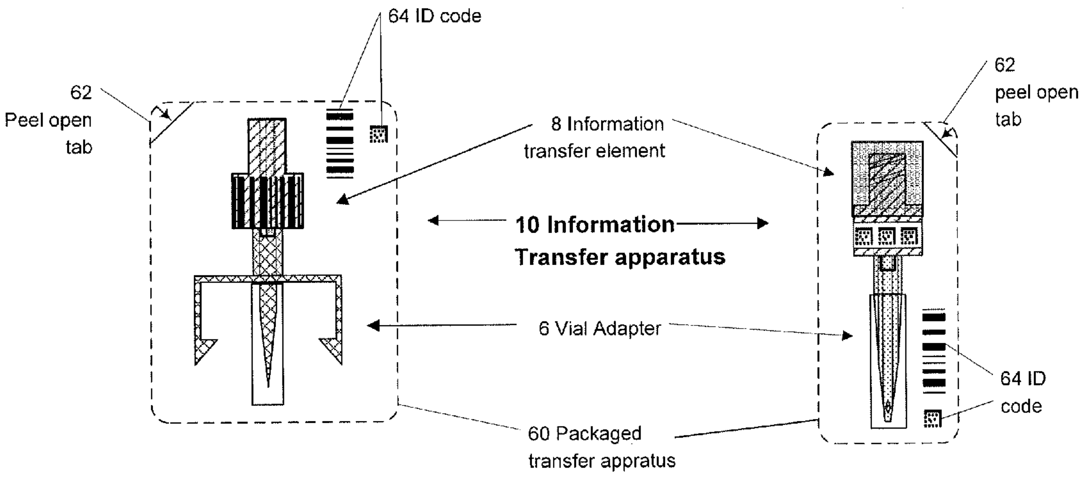
FIG. 5 is diagram illustrating a medication information transfer apparatus as in FIG. 1.
FIG. 6 is diagram illustrating an alternate medication information transfer apparatus as in FIG. 2.

FIG. 5 is diagram illustrating medication information transfer apparatus 10 as assembled for use. The assembly can be provided in package 60 with peel open tab 62 and ID code 64. ID code 64 can be provided on the outside of package 60 and can be directly related to the information contained in information source 58 inside. ID code 64 can be used by pharmaceutical company manufacturing personnel or equipment during the packaging of vial 4, by pharmacy or pharmacy services personnel or equipment during the kitting of vial 4 with information transfer apparatus 10, or by health care providers or equipment during the use of the medication in vial 4.

FIG. 6 is diagram illustrating a alternate medication information transfer apparatus 10 as assembled for use. The assembly can be provided in package 60 with peel open tab 62 and ID code 64. ID code 64 can be provided on the outside of package 60 and can be directly related to the information contained in information source 58 inside. ID code 64 can be used by pharmaceutical company manufacturing personnel or equipment during the packaging of vial 4, by pharmacy or pharmacy services personnel or equipment during the kitting of vial 4 with information transfer apparatus 10, or by health care providers or equipment during the use of the medication in vial 4.

Figure 7:
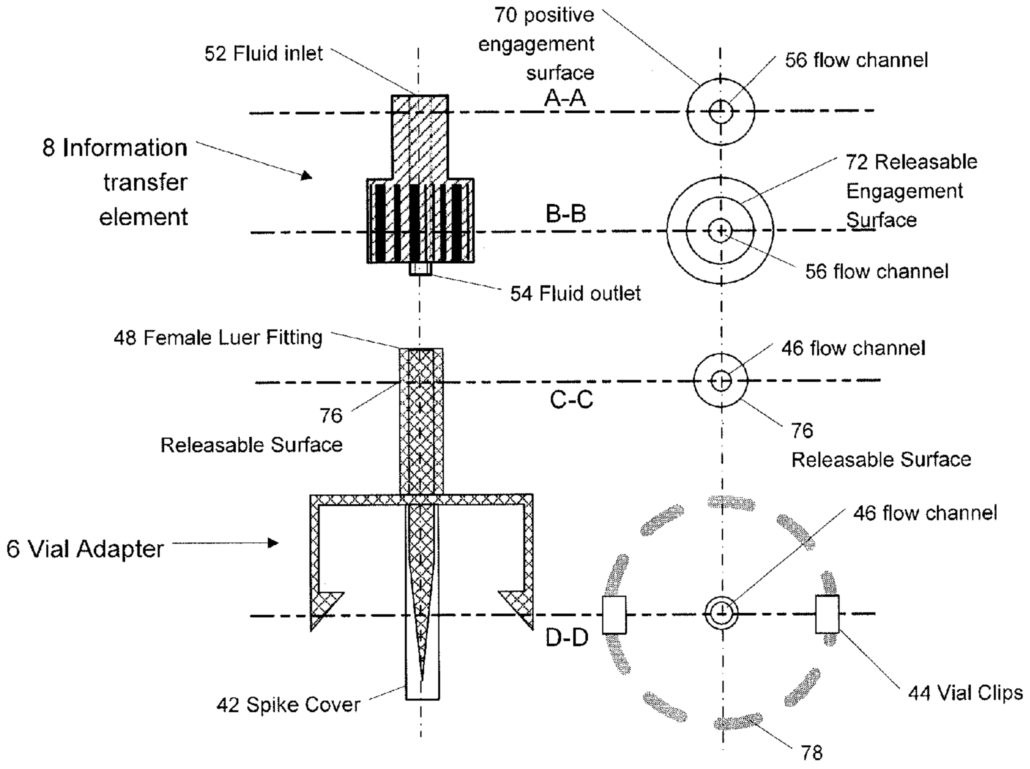
FIG. 7 is a diagram describing a detailed cross-sectional view of a medication information transfer apparatus as in FIG. 3.

FIG. 7 is a diagram describing a detailed cross-sectional view of medication information transfer apparatus 10 as in FIGS. 3 and 5. Sections A-A and B-B are of information transfer element 8. Section A-A shows the cross section of fluid inlet 52. Inside can be fluid flow channel 56 and outside can be positive engagement surface 70. Section B-B shows the cross section of fluid outlet 54. Inside can be fluid flow channel 56 and outside can be releasable engagement surface 72. Sections C-C and D-D are of vial adapter 6. Section C-C shows the cross section of female luer fitting 48. Inside can be flow channel 46 and outside can be releasable surface 76. Section D-D shows the cross section of the spike end of vial adapter 6. Inside can be vial flow channel 46 and outside can be vial clips 44. There can be two or more vial clips 44 located anywhere around circumference 78.

In one implementation of information transfer element 8, releasable engagement surface 72 and releasable surface 76 are easily detachable mating surfaces so as to allow disengagement. These surfaces can be smooth and do not promote a restrictive engagement when a user tries to disengage information transfer element 8 from vial adapter 6. Additionally, positive engagement surface 70 promotes a restrictive engagement with luer fitting 32 of syringe 12. If syringe 12 is a slip luer fitting 32 without a luer lock, the positive engagement surface 70 can be on the inner surface of the female slip luer fitting forming fluid inlet 52. If syringe 12 is a luer lock fitting, the outer surface of positive engagement surface 70 can be on the outer surface of the luer fitting forming fluid inlet 52. Information transfer element 8 can have one or both positive engagement surfaces 70. Positive engagement surface 70 can be one or more of a threaded surface, a knurled surface, a splined surface, an etched surface, a ribbed surface, etc.

Figure 8:
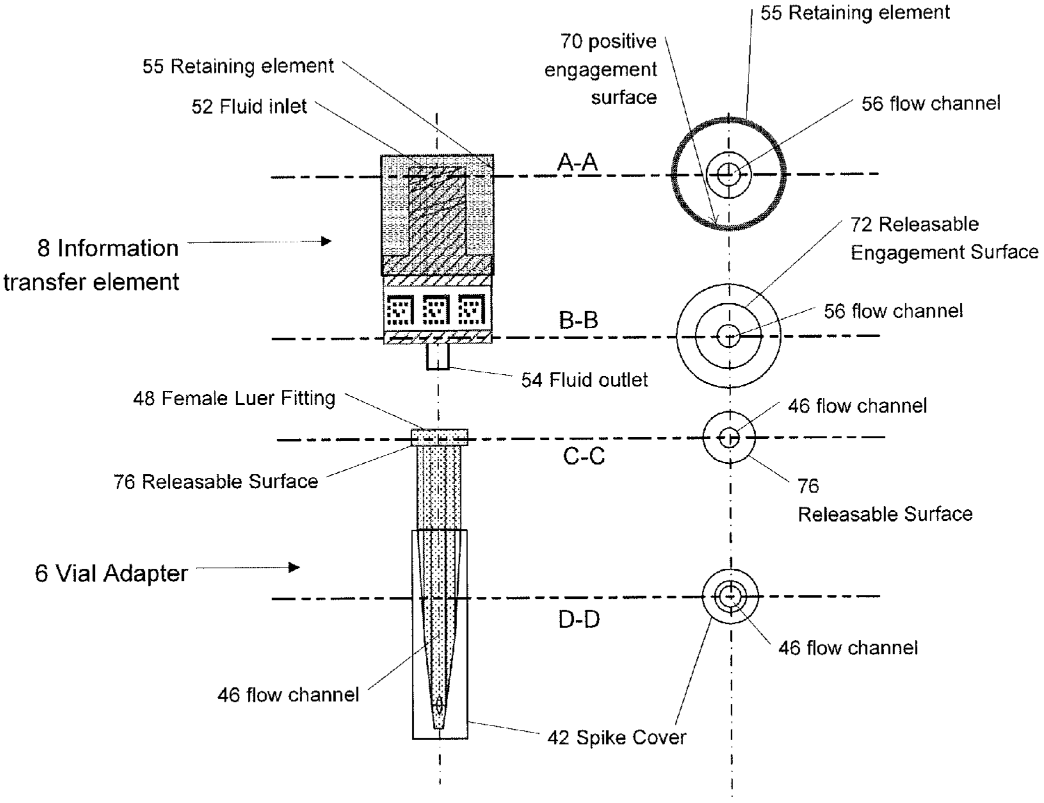
FIG. 8 is a diagram describing a detailed cross-sectional view of an alternate medication information transfer apparatus as in FIG. 4.

FIG. 8 is a diagram describing a detailed cross-sectional view of an alternate medication information transfer apparatus 10 as shown in FIGS. 4 and 6. Sections A-A and B-B are of information transfer element 8. Section A-A shows the cross section of fluid inlet 52. Inside can be fluid flow channel 56 and outside can be positive engagement surface 70 of retaining element 55. Section B-B shows the cross section of fluid outlet 54. Inside can be fluid flow channel 56 and outside can be releasable engagement surface 72. Sections C-C and D-D are of vial adapter 6. Section C-C shows the cross section of female luer fitting 48. Inside can be flow channel 46 and outside can be releasable surface 76. Section D-D shows the cross section of the spike end of vial adapter 6. Inside can be vial flow channel 46 and outside can be spike cover 42. Flow channel 46 can terminate with a pointed end for penetrating a rubber vial closure or IV bag injection port.

In one implementation of information transfer element 8, releasable engagement surface 72 and releasable surface 76 are easily detachable mating surfaces so as to allow disengagement. These surfaces can be smooth and do not promote a restrictive engagement when a user tries to disengage information transfer element 8 from vial adapter 6. Additionally, positive engagement surface 70 can promote a restrictive engagement with luer fitting 32 or luer lock hub 33 of syringe 12. If syringe 12 is a slip luer fitting 32 without a luer lock, the positive engagement surface 70 can be on the inner surface of the female slip luer fitting forming fluid inlet 52. If syringe 12 is a luer lock fitting, the inner surface of positive engagement surface 70 can be on the inner surface of retaining element 55. In this variation, the outer surface of syringe 12 luer lock hub 33 will couple and positively engage with the inner surface of retaining element 55. Information transfer element 8 can have one or both positive engagement surfaces 70.

Figure 9:
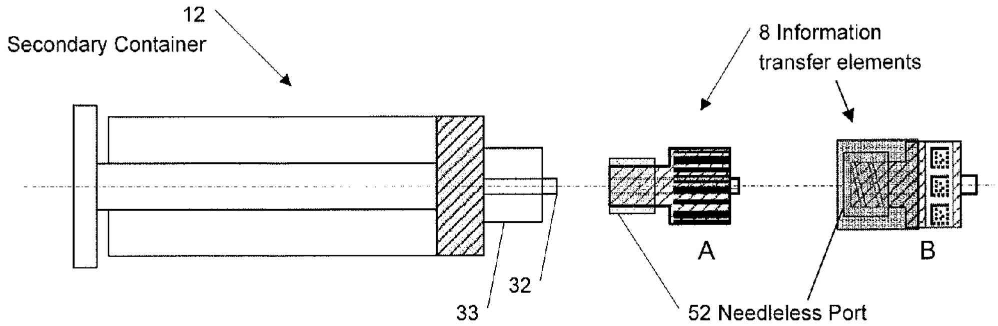
FIGS. 9 and 10 are diagrams illustrating two variations of a syringe connection to an information transfer element as in FIGS. 3 and 5.
Figure 10:
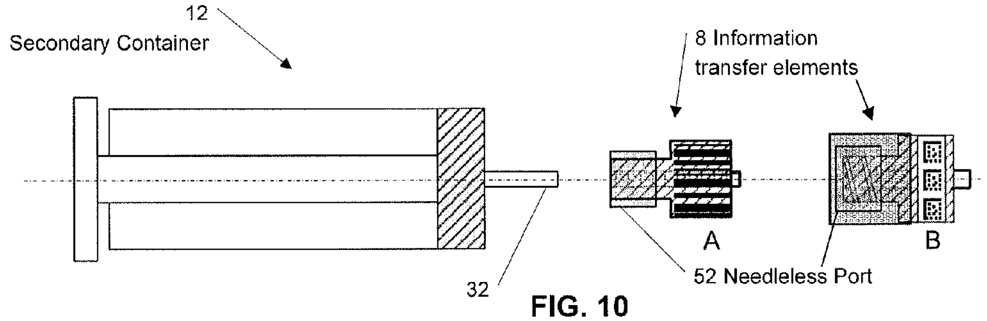

There may be need for multiple medication withdrawals required from vial 4 containing a multi-dose volume of medication 20. FIGS. 9, 10, 11 and 12 depict the use of needleless access devices that can provide easy luer fitting and fluid access. FIGS. 9 and 10 depict information transfer element 8 with fluid inlet 52 configured as a needleless access port allowing multiple engagements of syringe 12 without the need for needles. FIG. 9 shows a luer lock type syringe hub 33 and FIG. 10 shows a luer slip type syringe tip 32. Each can access needleless access port 52 allowing multiple engagements of information transfer element 8. Alternatively as shown to the right in FIGS. 9 and 10, information transfer element 8 can include a needleless port 52.

Further, there can also be need for multiple medication withdrawals required from vial 4 containing a multi-dose volume of medication 20 where each withdrawal can be completed using a separate syringe 12 each having its own information transfer element 8.

Figure 11:
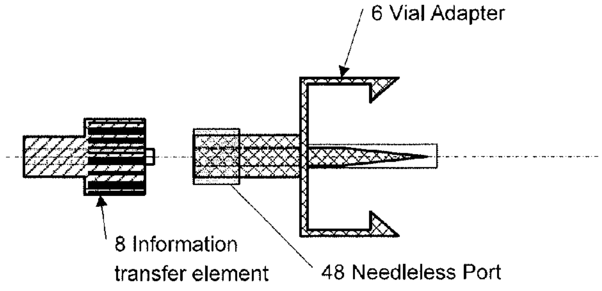
FIG. 11 depicts a variation of an information transfer element connection with a vial adapter as in FIG. 3.
Figure 12:
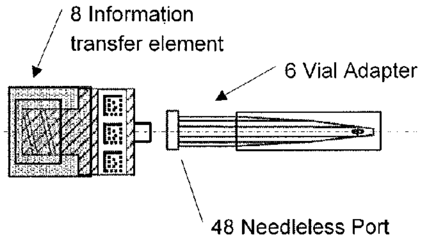
FIG. 12 depicts a variation of an alternate information transfer element connection with a vial adapter as in FIG. 4.

FIGS. 11 and 12 depict vial adapter 6 with female luer fitting 48 configured as a needleless access port allowing multiple engagements of information transfer element 8.

Figure 13:
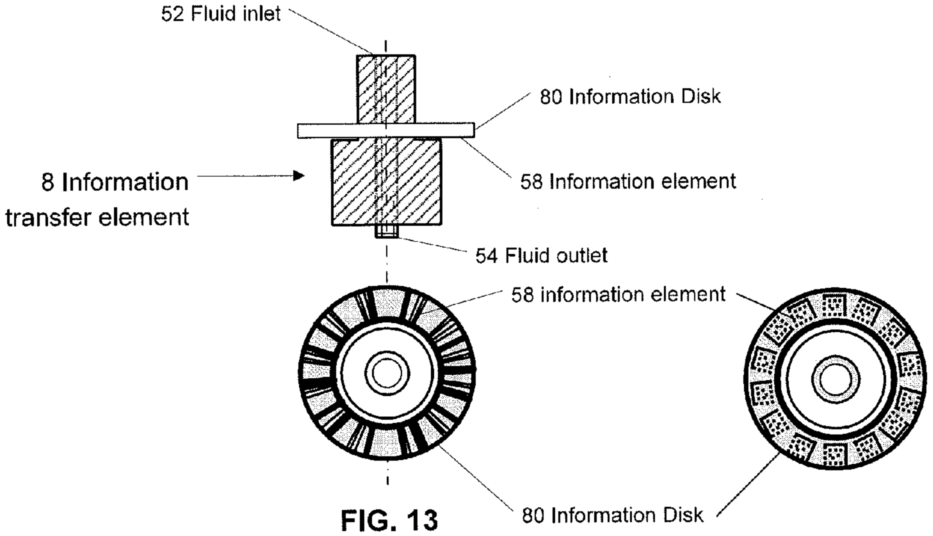
FIG. 13 is a diagram illustrating an information element as a disc.
Figure 14:
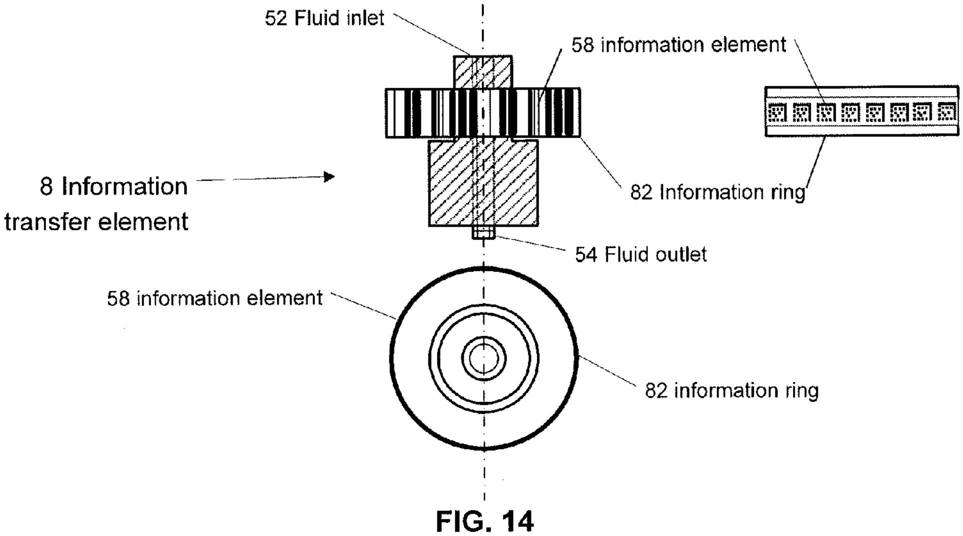
FIG. 14 is a diagram illustrating an information element as a ring.

FIGS. 13 and 14 depict an information element 58 as a circular disk or ring. FIG. 13 depicts information transfer element 8 with a flat information disk 80. Information element 58 can be on a planar and annular portion of an underside of disk 80. FIG. 14 depicts information transfer element 8 with information ring 82. Information element 58 can be on a curved cylindrical outer surface of ring 82.

Figure 15:
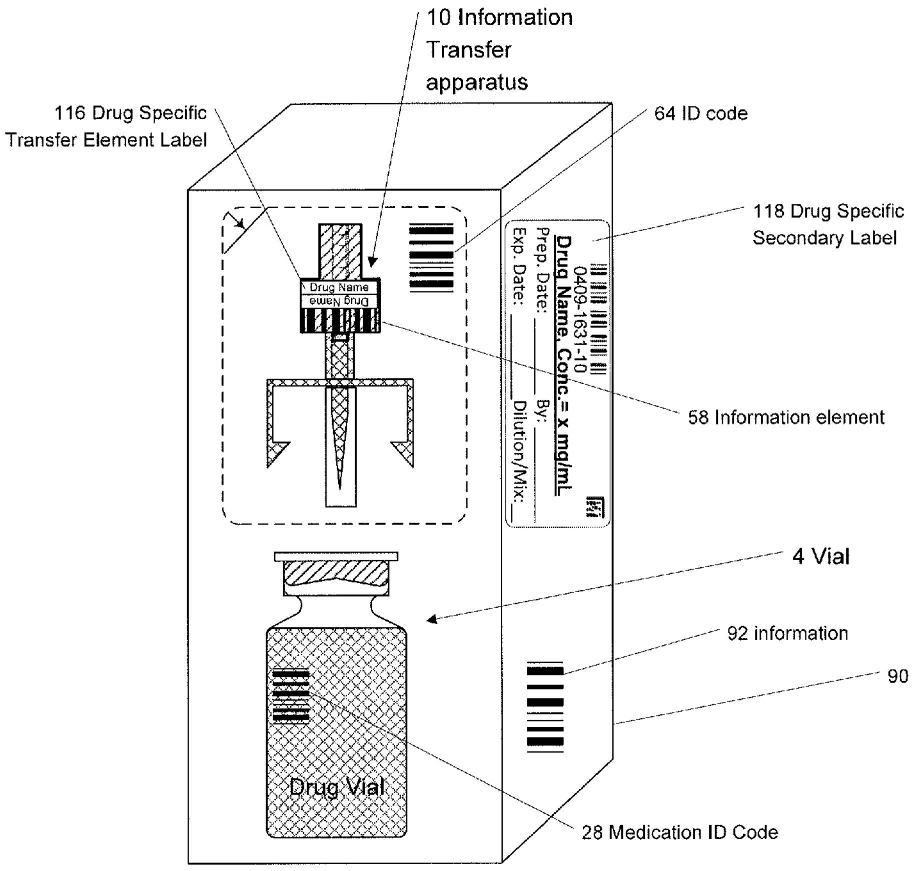
FIG. 15 is a diagram illustrating a first alternate packaging configuration.

FIGS. 15 through FIG. 23 depict alternate implementations of packaging and labeling. FIG. 15 depicts a first alternate packaging configuration that can be completed by a pharmaceutical manufacturer. In this variation, vial 4 can be packaged together with information transfer apparatus 10 in container 90. Various labeling and instructions for use (not shown) about the medication can be printed on or contained within container 90 including information 92 indicative of the contents of vial 4. Here the pharmaceutical manufacture checks and verifies that medication ID code 28, information 92, information element 58 and ID code 64 all match and/or are in agreement.

Figure 16:
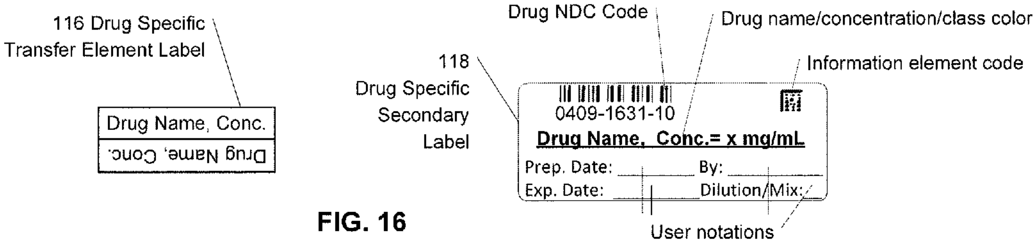
FIG. 16 is a diagram illustrating human readable labels.

FIG. 16 depicts human readable labels. Information transfer apparatus 10 can include human readable information about the medication including, but not exclusive of drug specific transfer element label 116 and drug specific secondary label 118. Label 116 to the left can include the drug name and concentration or other information indicative of the medication in vial 4 and be either right side up or upside down or both. Label 116 can include drug classification color(s) as indicated in the "ASTM D4774-06 Standard Specification for User Applied Drug Labels in Anesthesiology". Drug specific secondary label 118 to the right can be provided with an adhesive backing for attachment to secondary container 12 (syringe) and include any one or more of the drug name, concentration, drug NDC barcode and number, information element code, and user notations including but not exclusive of preparer's name/initials, preparation date/time, expiration date/time, indication of dilution, indication of mixing, storage instructions (protect from light, refrigerate, etc.), patient ID/name, medication administration instructions, warnings. Similarly, label 118 can include drug classification color(s) as indicated in the "ASTM D4774-06 Standard Specification for User Applied Drug Labels in Anesthesiology" or other industry/clinical labeling standards.

Figure 17:
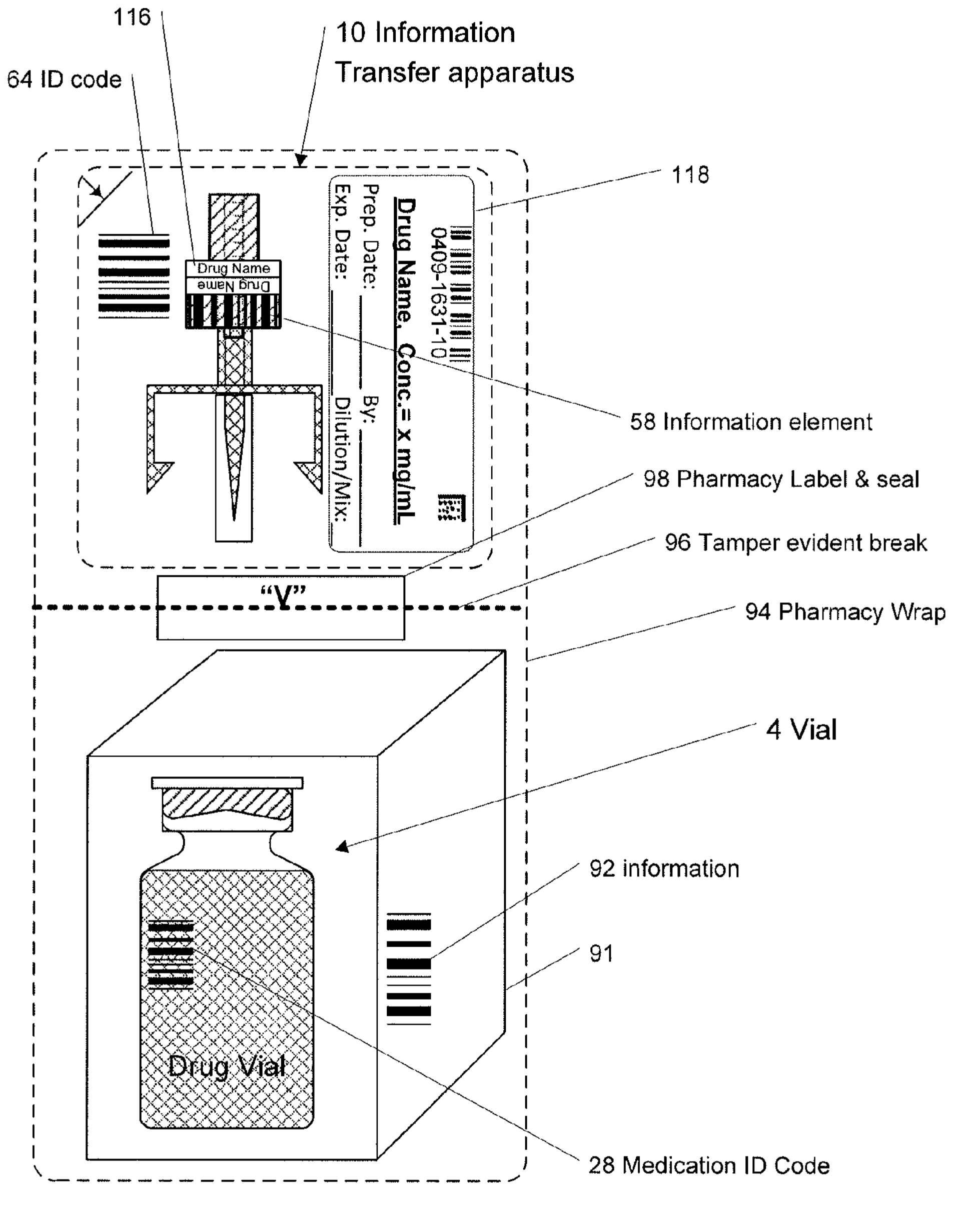
FIG. 17 is a diagram illustrating a second alternate packaging configuration.

FIG. 17 depicts a second alternate packaging configuration completed by a pharmacy or pharmaceutical services company. In this variation, vial 4 can be packaged in container 91 by the pharmaceutical manufacturer. Various labeling and instructions for use (not shown) about the medication can be printed on or contained within container 91 including information 92 indicative of the contents of vial 4. The pharmacy or pharmacy services provider can package together vial 4 and information transfer apparatus 10 into pharmacy wrap 94. Pharmacy wrap 94 can have a tamper evident break point 96 and pharmacy seal 98 to provide assurance of package integrity. In this variation the pharmacy can check and verify that information 92, medication ID code 28 and ID code 64 match and/or are in agreement. Pharmacy label 98 can be an indication of this verification check ("V"). Additionally, drug specific label 116 can be part of information transfer apparatus 10 providing a human readable indication of the medication type and concentration. Additionally, drug specific secondary label 118 can be part of the information transfer apparatus 10 providing a secondary label for syringe 12.

Figure 18:
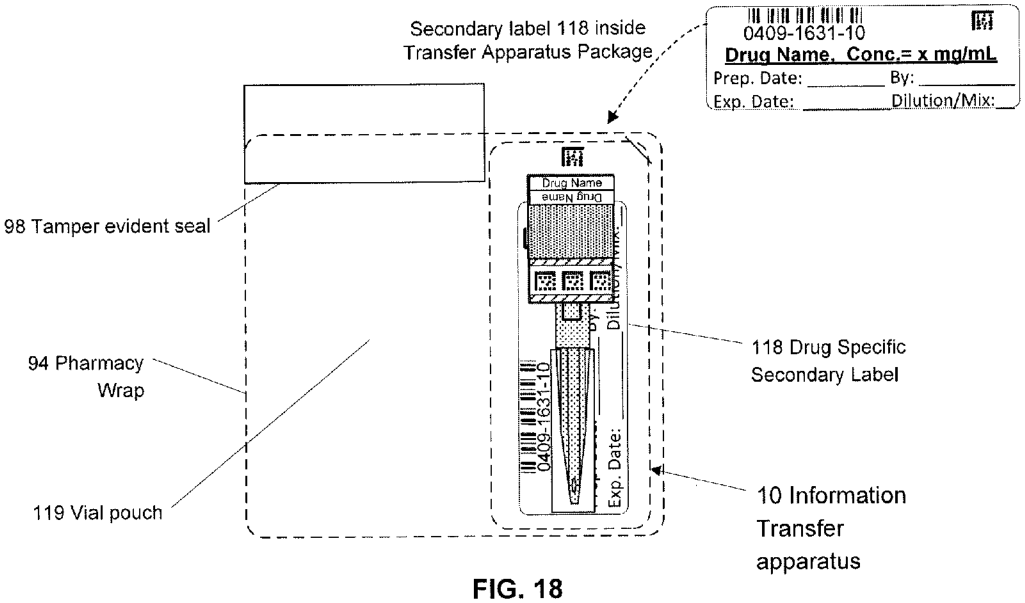
FIG. 18 is a diagram illustrating a third alternate packaging configuration with an alternate information transfer apparatus without a vial.
Figure 19:
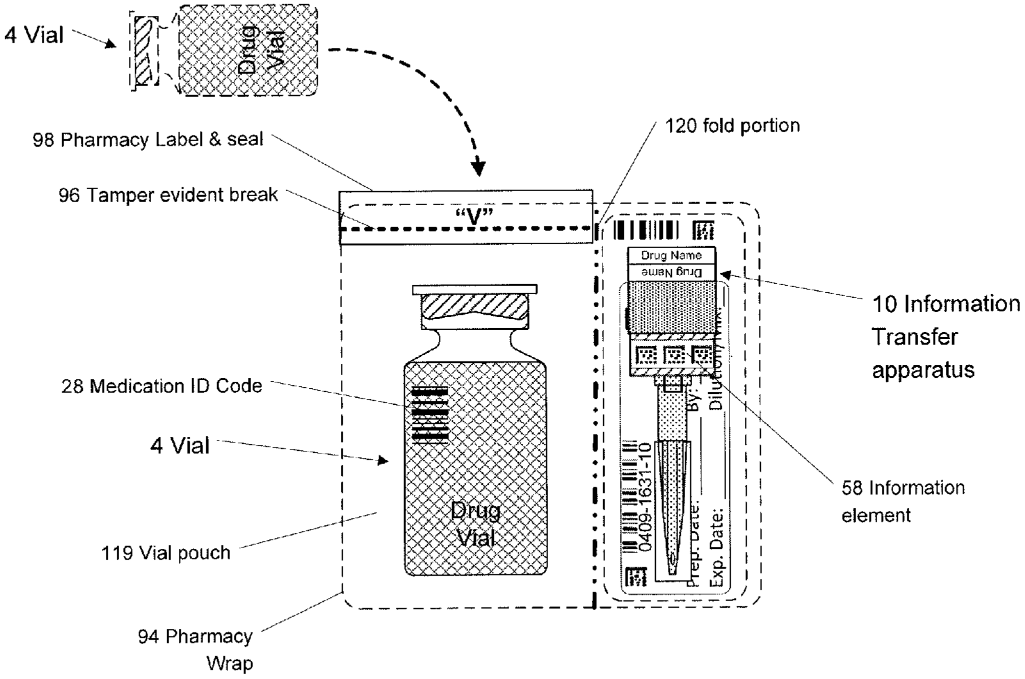
FIG. 19 is a diagram illustrating a third alternate packaging configuration with an alternate information transfer apparatus with a vial.

FIGS. 18 and 19 are diagrams illustrating a third alternate packaging configuration with an alternate information transfer apparatus as in FIGS. 4 and 6. FIG. 18 depicts pharmacy wrap 94 that can be in the form of a flexible sterile package with at least two pouches. On the right, information transfer apparatus 10 is provided inside a sealed pouch with label 118 and can be sterilized. On the left is an open unfilled vial pouch 119 available for filling with vial 4. Pharmacy wrap 94 can include an un-sealed tamper evident seal 98. Alternatively, there can be more than one vial pouch 119 provided for use with more than one vial (see FIG. 30). In this variation, there can be more than one tamper evident seal 98 and more than one indication of verification "V".

FIG. 19 illustrates the insertion of vial 4 into empty vial pouch 119. Vial 4 and information transfer element 10 are verified by a pharmacy person and tamper evident seal 98 is sealed. Similar to that shown in FIGS. 15 and 16, medication ID code 28 must be in agreement with information element code 58. A "V" mark or other indication of verification can be placed on pharmacy seal 98. A tamper evident break 96 can be included to indicate if the pharmacy seal has been broken. Pharmacy wrap 94 can have a foldable portion 120 allowing information transfer apparatus 10 to fold in-front of or behind vial 4 and pouch 119 thus conserving storage space.

Figures 20, 21, 22:
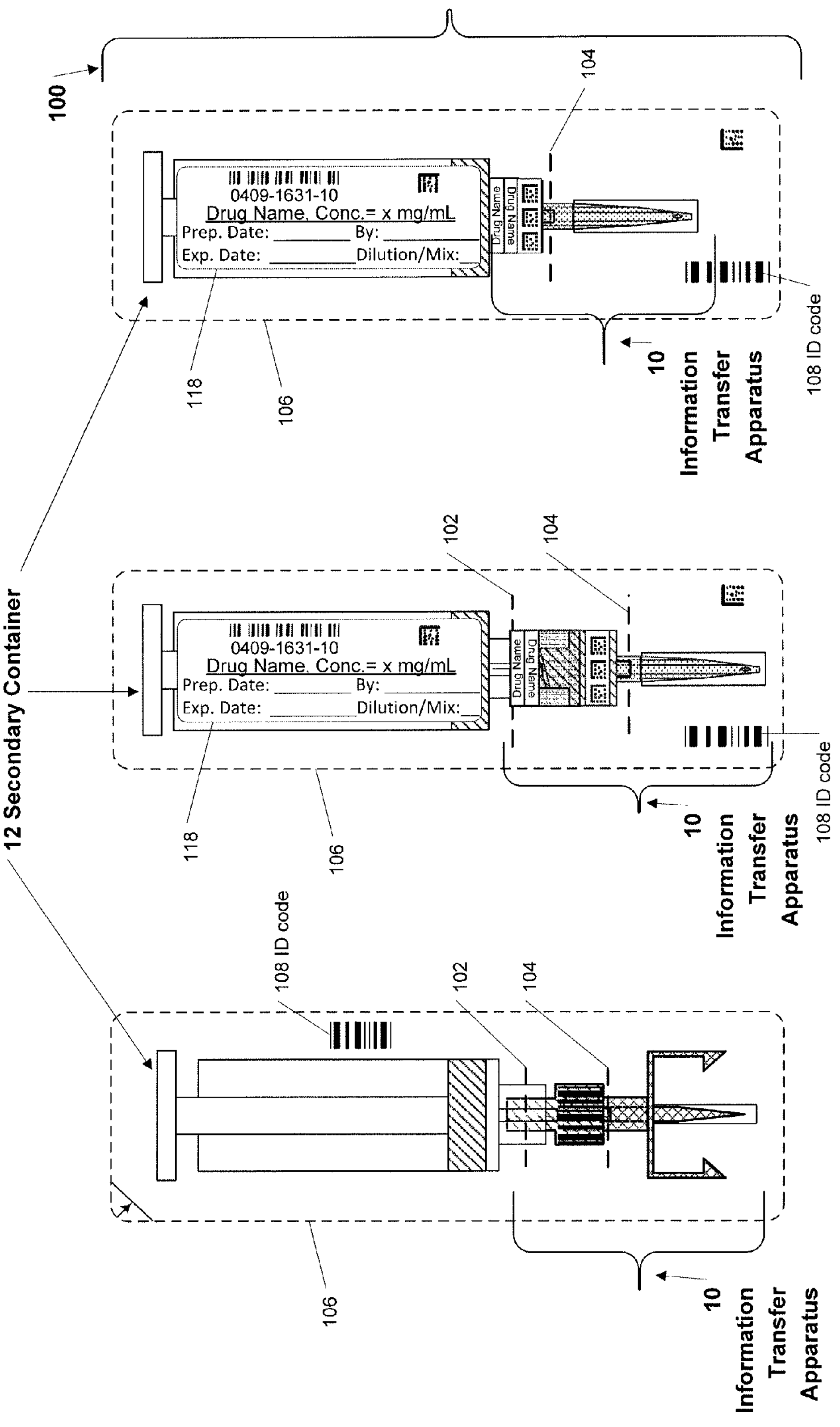
FIG. 20 is a diagram illustrating a fourth alternate packaging configuration.
FIG. 21 is a diagram illustrating a fifth alternate packaging configuration with an alternate information transfer apparatus.
FIG. 22 is a diagram illustrating a sixth alternate packaging configuration with an integrated information transfer apparatus.

FIGS. 20, 21 and 22 depict a fourth, fifth and sixth alternate packaging configurations. In this variation, a manufacturer can join secondary container 12 to transfer apparatus 10 forming assembly 100. The assembly 100 can be affixed together (bonded, snapped, latched, threaded, etc.) at point 102 such that separation is limited. In this affixed case, point 104 remains easily separable by the health care provider during use. Further, assembly 100 can be packaged in pouch 106, marked with ID code 108 and sterilized. The sterilized packaged assembly 100 can be provided to the health care provider for use. FIGS. 20 and 21 show information transfer apparatus 10 pre-assembled with a secondary container. FIG. 22 shows an integrated secondary container 12 with information transfer apparatus 10. In another alternative similar to FIG. 22, secondary container 12 can be integrated with information transfer element 8 and vial adapter 6 provided separately. Note, that in these variations, vial 4 is provided to the health care provider separately. Similar to FIG. 17, a pharmacy or pharmacy services provider can package vial 4 and assembly 100 into pharmacy wrap 94 with tamper evident break point 96 and seal 98.

Figure 23:
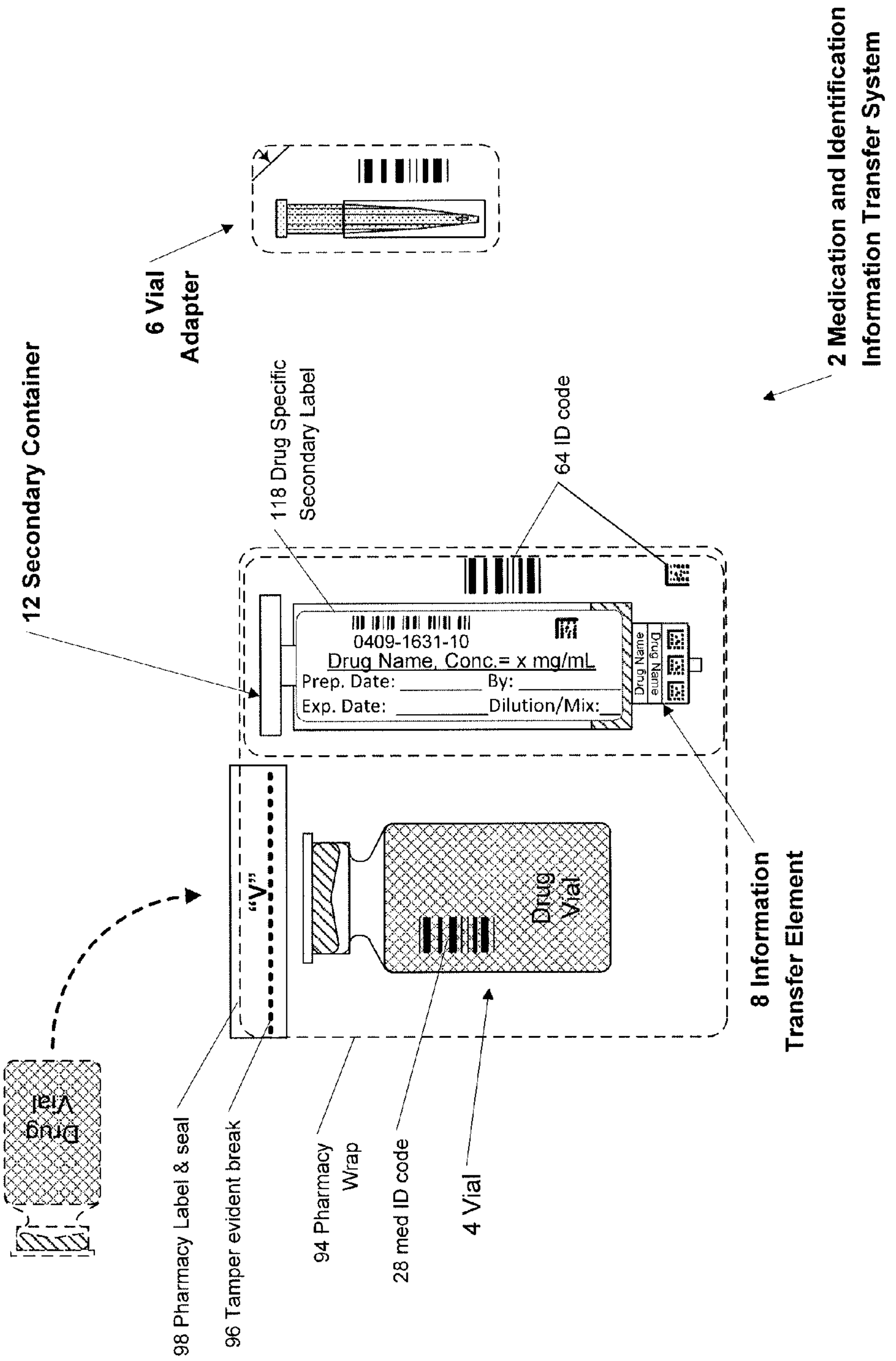
FIG. 23 is a diagram illustrating a seventh alternate packaging configuration with an integrated information transfer element with a vial.

FIG. 23 depicts a seventh alternate packaging configuration. In this variation the secondary container 12 is packaged with the information transfer apparatus 10 fully integrated with secondary container 12 including vial 4. Vial 4 can be put into the pharmacy wrap 94 and sealed by pharmacy seal 98. Medication ID code 28 can be verified as being in agreement with ID code 64. Label 118 can be pre-attached to secondary container 12. In this variation vial adapter 6 is provided separately.

Figure 24:
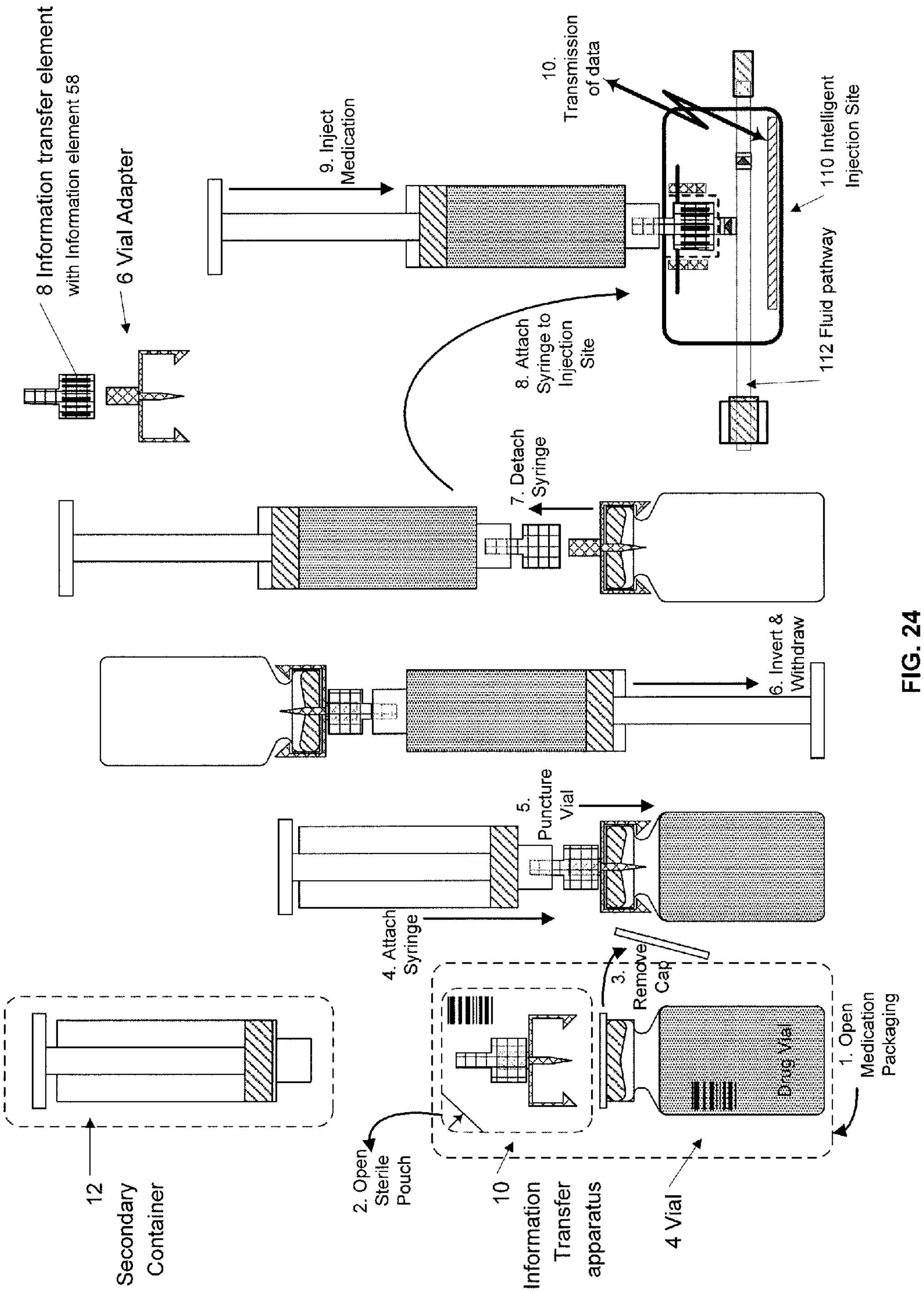
FIG. 24 is a diagram illustrating a sequence of steps describing the use of medication and identification information transfer system as in FIG. 1.

FIG. 24 is a diagram illustrating a sequence of steps describing the use of medication and identification information transfer system 2. The following steps are numbered in sequence and generally progress from left to right:

1. Open package and remove vial 4 and information transfer apparatus 10.
2. Open information transfer apparatus 10 package and remove information transfer apparatus 10.
3. Remove flip-off cap 26 from vial 4.
4. Remove syringe 12 from its sterile pouch and attach to information transfer apparatus 10.
5. Attach information transfer apparatus 10 to vial 4 by puncturing vial 4's rubber closure 24 with spike 40.
6. Invert vial 4 and information transfer apparatus 10 and withdraw medication 20 from vial 4 by pulling on plunger rod 32.
7. Detach syringe 12 with information transfer element 8 from vial adapter 6 and vial 4.
8. Attach syringe 12 with information transfer element 8 to intelligent injection site 110.
9. Inject medication 20 into injection site 110 and fluid pathway 112.
10. Medication information is transmitted by intelligent injection site 110 to a data collection system (not shown). Features and functions of intelligent injection site 110, fluid pathway 112 and the data collection system are described in U.S. patent application Ser. Nos. 12/614,276, 12/765,707 and 12/938,300 all entitled "Medication Injection Site and Data Collection System".

Figure 25:
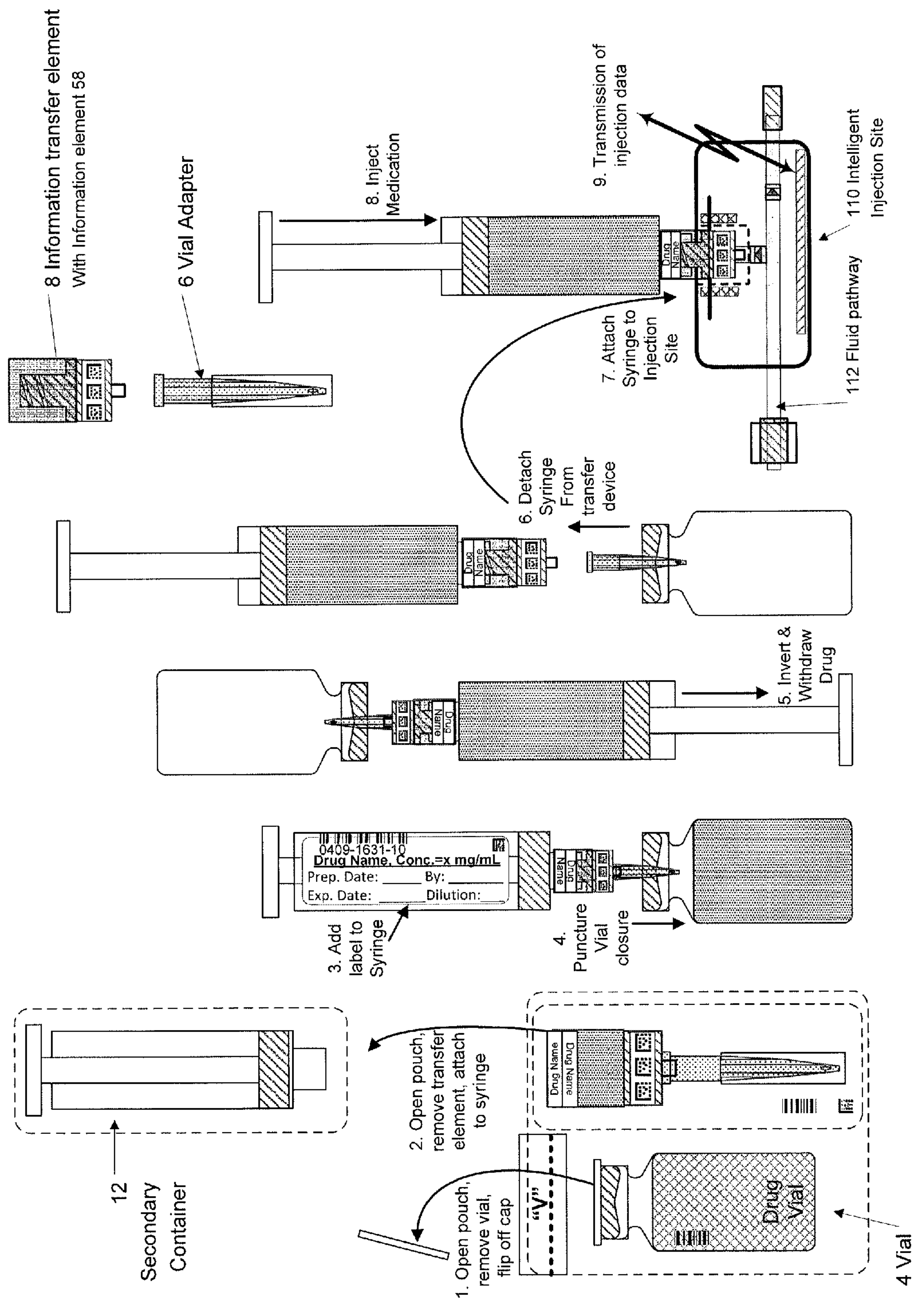
FIG. 25 is a diagram illustrating a sequence of steps describing the use of an alternate medication and identification information transfer system as in FIG. 2.

FIG. 25 is a diagram illustrating a sequence of steps describing the use of an alternate medication and identification information transfer system 2 as in FIG. 19. The following steps are numbered in sequence and generally progress from left to right:

1. Open vial pouch package 119 (left), remove vial 4 and flip off vial cap 26.
2. Open information transfer apparatus 10 pouch (right), remove information transfer apparatus 10 and attach secondary container 12 to transfer apparatus 10.
3. Affix drug specific secondary label 118 to secondary container 12.
4. Attach information transfer apparatus 10 to vial 4 by puncturing vial 4's rubber closure 24 with spike 40.
5. Invert vial 4, secondary container 12 and information transfer apparatus 10 and withdraw medication 20 from vial 4 by pulling on plunger rod 32.
6. Invert again and detach secondary container 12 with information transfer element 8 from vial adapter 6 and vial 4.
7. Attach secondary container 12 with information transfer element 8 to intelligent injection site 110.
8. Inject medication 20 into injection site 110 and fluid pathway 112.
9. Medication information is transmitted by intelligent injection site 110 to data collection system (not shown). Features and functions of intelligent injection site 110, fluid pathway 112 and data collection system are described in U.S. patent application Ser. Nos. 12/614,276, 12/765,707 and 12/938,300 all entitled "Medication Injection Site and Data Collection System".

Figure 26:
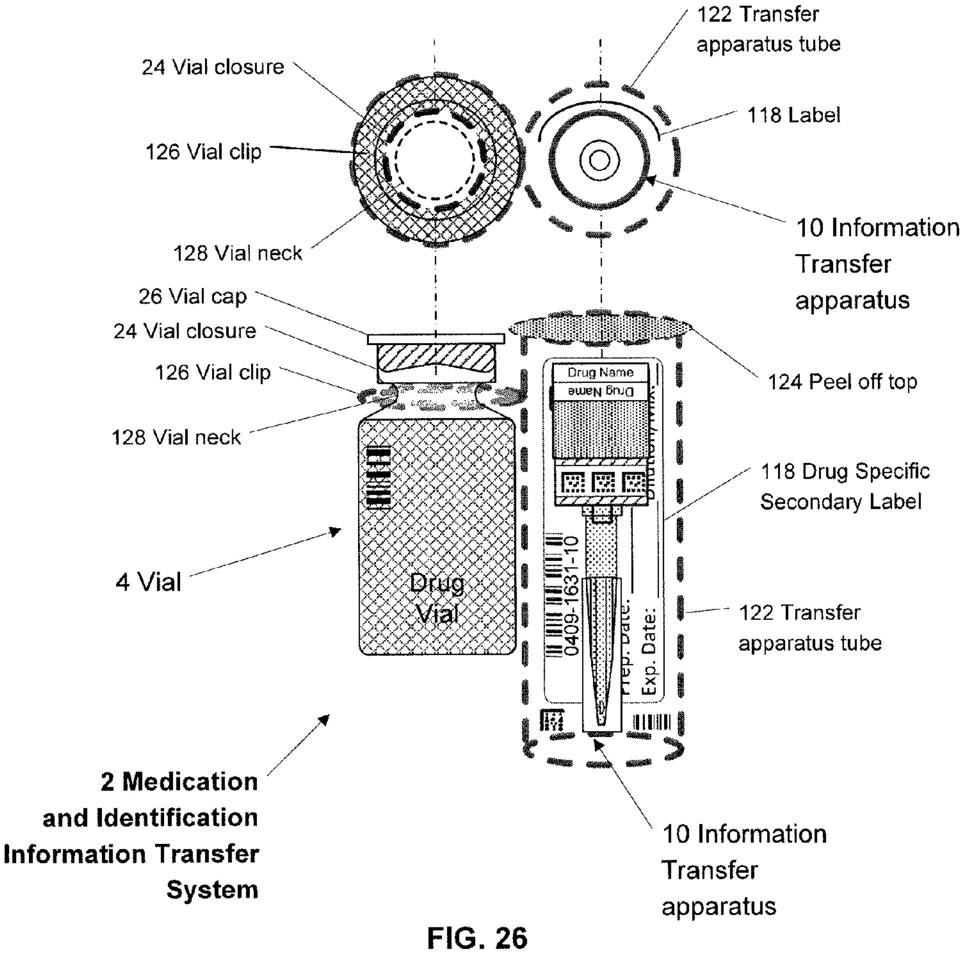
FIG. 26 is a diagram illustrating a eighth packaging configuration with an alternate medication and identification information transfer apparatus with a vial as in FIG. 2.

FIG. 26 is a diagram illustrating an eighth alternate packaging configuration with an alternate information transfer apparatus with a vial as in FIG. 2. Information transfer apparatus 10 can be packaged in tube 122 with label 118 and sealed closed with top 124. Sealed tube 122 can be sterilized. Tube 122 can have vial clip 126 that slips over vial cap 26 and vial closure 24 and is retained on vial neck 128. Vial clip 126 can comprise a clip, elastic band, shrink-wrap, adhesive tape, or other mechanism for affixing vial 4 to transfer apparatus tube 122. Alternatively, vial clip 126 can slip under vial 4 so as not to disturb cap 26. Both assembly methods result in vial clip 126 securing vial 4 at vial neck 128. In this packaging configuration secondary container 4 can directly access and attach to information transfer apparatus 10 while still in tube 122. Information transfer apparatus 10 can be provided separately from vial 4. Vial 4 can be attached to transfer tube 122 by a pharmacy or pharmacy services supplier. Once the vial clip 126 has retained vial 4 at neck 128 there is no need to remove it. Cap 26 can be flipped off and vial adapter 6 spike 40 can penetrate the vial closure 24, withdraw medication 20 and secondary container 12 can detach from vial adapter 6. Secondary label 118 can be applied to secondary container 12 (not shown).

Figure 27:
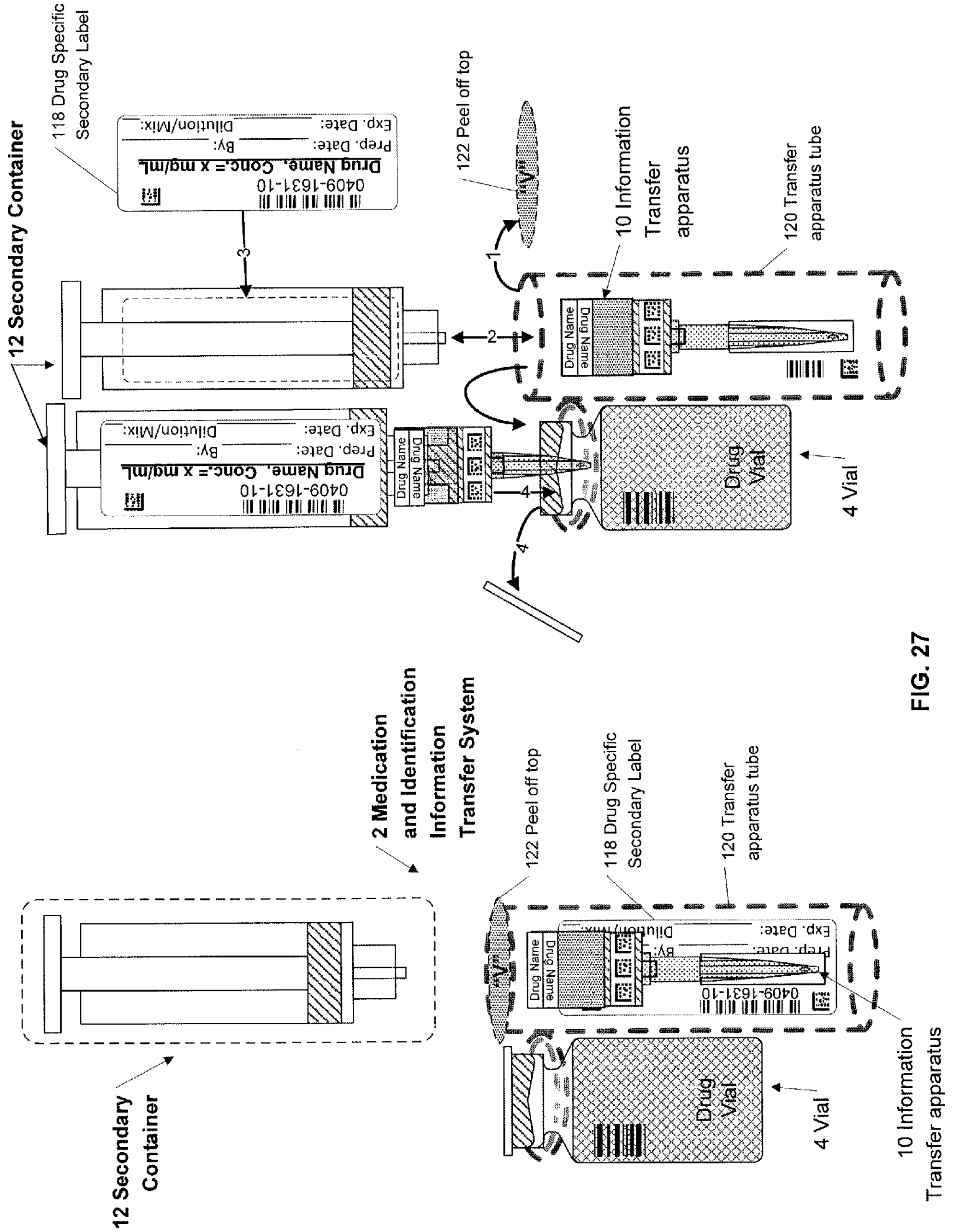
FIG. 27 is a diagram illustrating a sequence of steps describing the use of medication and identification information transfer system as in FIG. 26.

FIG. 27 is a diagram illustrating a sequence of steps describing the use of medication and identification information transfer system as in FIG. 26. On the right are steps describing the use of the system and are numbered in sequence: Shown to the left is the packaged system 2.

1. Secondary container 12 (syringe) is removed from its sterile packaging and peel off top 122 is removed from tube 120.
2. Syringe 12 can enter tube 120, attach to and remove transfer apparatus 10.
3. Syringe label 118 can be attached to the empty syringe 12.
4. Vial cap 26 is flipped off and vial adapter 6 spike 40 can penetrate vial closure 24 to access the medication.
5. The assembly is inverted and plunger rod 32 is pulled to withdraw medication 20 from vial 4 (not shown).
6. Syringe 12 with medication 20 can be attached to a medication port for medication administration (not shown).

Figure 28:
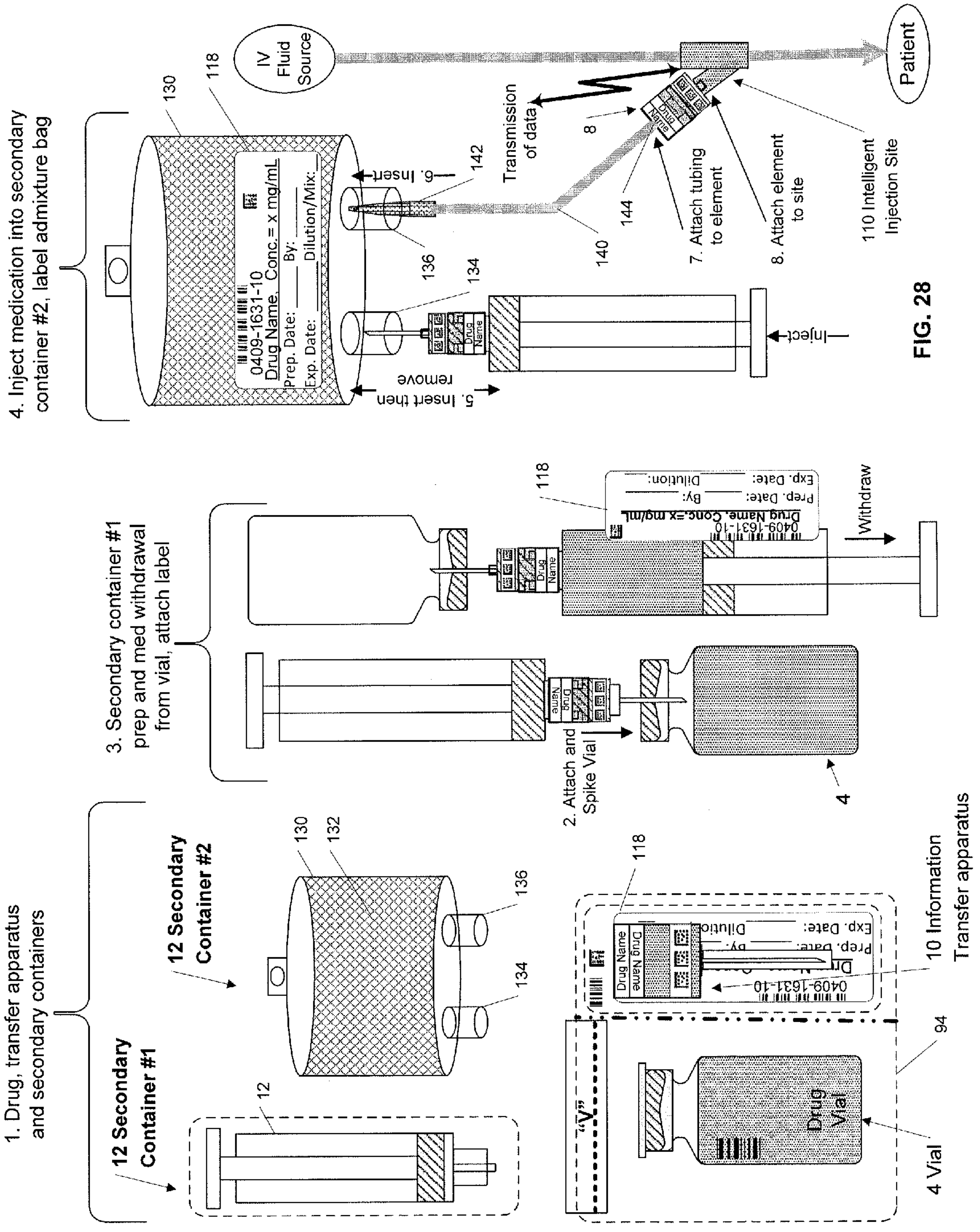
FIG. 28 is a diagram illustrating a medication and identification information transfer system used with an IV admixture bag.

FIG. 28 is a diagram illustrating a medication and identification information transfer system 2 used with an IV admixture bag. The same system 2 can be used for adding medication to a IV admixture bag 130 or bottle (not shown). Medication in vial 4 can be accessed in a similar manner as described above using secondary container #1 (syringe) 12 and information transfer apparatus 10. In this variation a second secondary container #2 130 (an IV admixture bag or bottle) can contain solution 132 (typically saline, sterile water, dextrose 5% in water, ringers lactate, or other diluent solution). These admixture bags 130 are typically provided in 50 mL to 250 mL sterile fluid volumes. In this figure the vial adapter 6 is shown as a needle. The following steps are numbered in sequence and generally progress from left to right:

1. The care provider acquires the supplies: drug vial 4 packaged with transfer apparatus 10, secondary container #1 12, secondary container #2 130 and IV administration tubing set 140 (not shown).
2. Secondary container #1 12 is prepared and attached to information transfer apparatus 10.
3. Vial 4 is spiked, inverted and medication withdrawn by pulling on plunger rod 32. Label 118 is removed from the pharmacy wrap 94 and temporarily attached to secondary container #1 for syringe identification.
4. The healthcare provider removes the spike from vial 4 and takes secondary container #1 12 with vial adapter 6 and spikes it into admixture port 134 on admixture bag 130. The medication is then injected into secondary container #2 bag 130. Label 118 is transferred from secondary container #1 12 to bag 130 (secondary container #2) identifying the added medication on bag 130.
5. Empty secondary container #1 (syringe 12) is removed from port 134 and spike 40 is recapped with cover 42 to minimize contamination (not shown).
6. Proximal end 142 of IV tubing set 140 is spiked into port 136.
7. Syringe 12 is removed from transfer apparatus 10 and distal end 144 of tubing set 140 is attached to the female inlet of information transfer element 8.
8. Vial adapter 6 is removed from information transfer element 8. Information transfer element 8 is connected to intelligent injection site 110.
9. Information element 58 transfers medication information to injection site 110 and it in turn transmits data to a data collection system (not shown). Injection of medication is initiated by the healthcare provider. Note: The injection site can be part of a fluid delivery line from an IV source to the patient.

Figure 29:
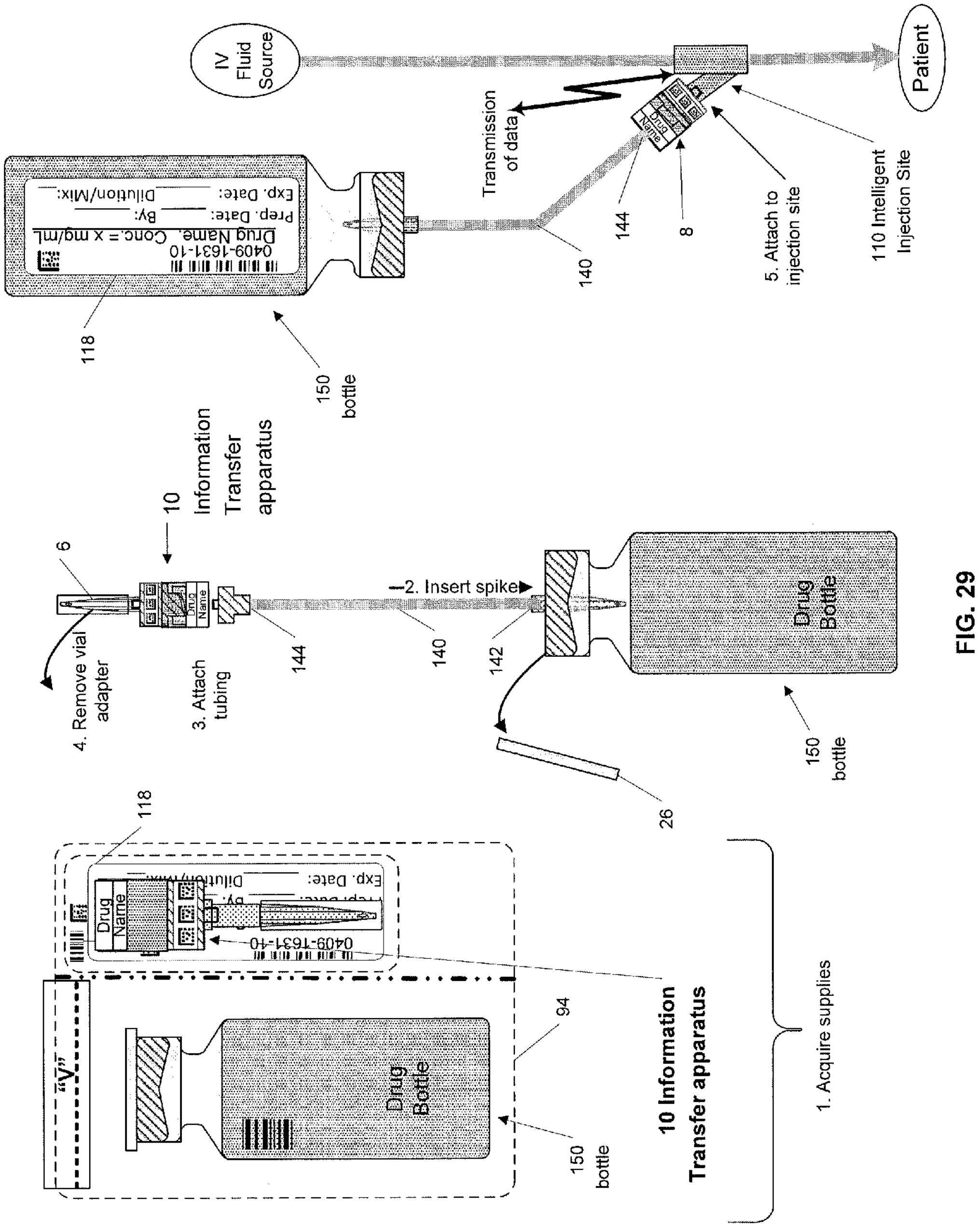
FIG. 29 is a diagram illustrating a medication and identification information transfer system used with an IV bottle.

FIG. 29 is a diagram illustrating a medication and identification information transfer system used with medication in an IV bottle. Some medications are provided in bottles instead of vials. In this variation a bottle of medication 150 can be prepared for use with IV tubing set 140. The following steps are numbered in sequence:

1. The health care provider acquires the supplies: drug bottle 150, transfer apparatus 10, and IV administration tubing set 140 (not shown).
2. IV tubing set 140 with proximal end spike 142 is inserted into drug bottle 150.
3. Using secondary container 12 (IV set 140), the distal end 144 is joined with information transfer apparatus 10. Label 118 is attached to drug bottle 150 to identify the medication and allow the healthcare provider to enter when and by whom the bottle was attached to the IV tubing 140.
4. Vial adapter 6 is removed from information transfer apparatus 10.
5. Information transfer element 8 with tubing 140 is connected to intelligent injection site 110.
6. Information element 58 transfers medication information to injection site 110 and it in turn transmits data to a data collection system (not shown). Note: The injection site can be part of a fluid delivery line from an IV source to the patient.

Figure 30:
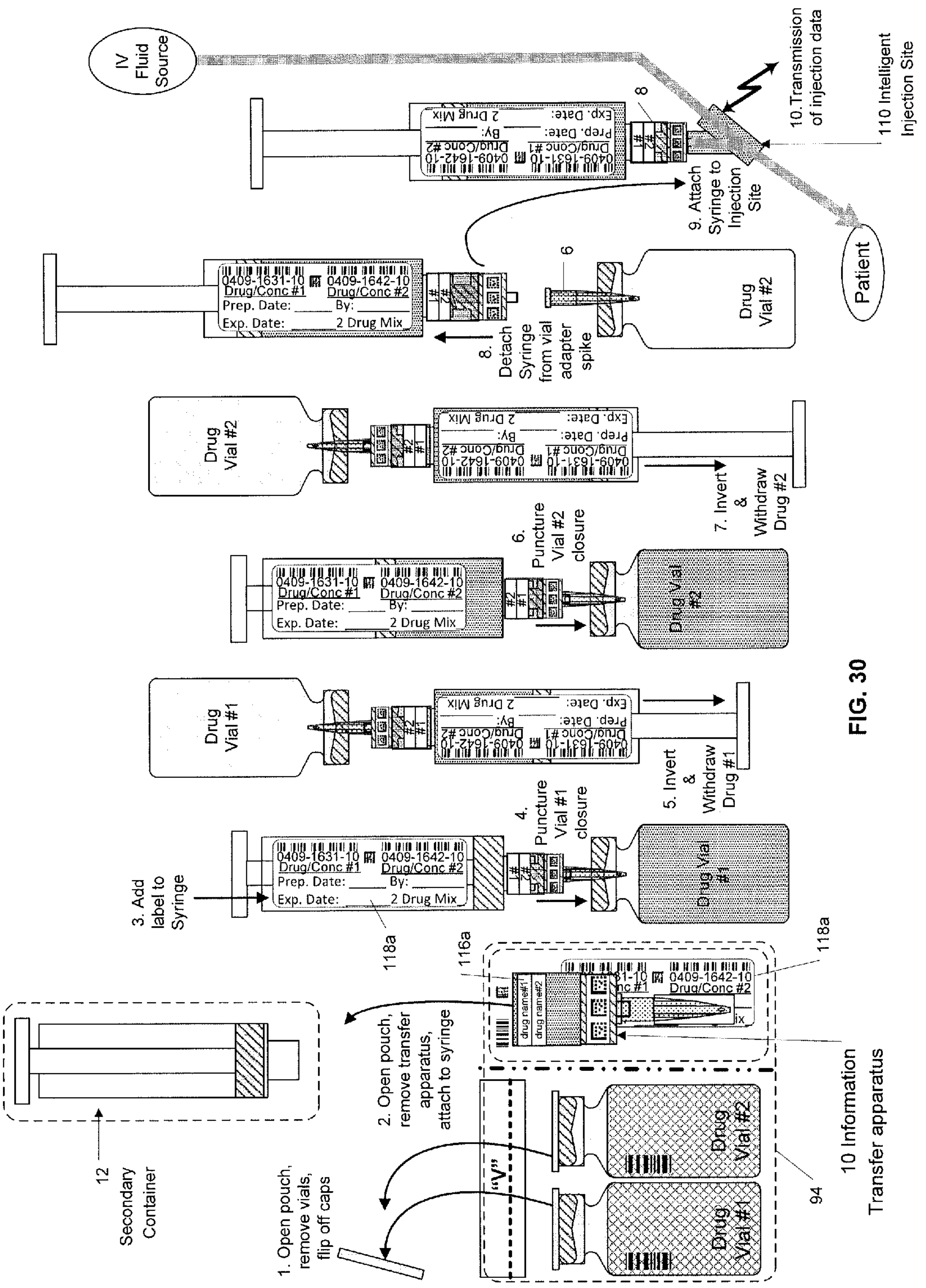
FIG. 30 is a diagram illustrating a medication and identification information transfer system used with two medications.
Figure 31:
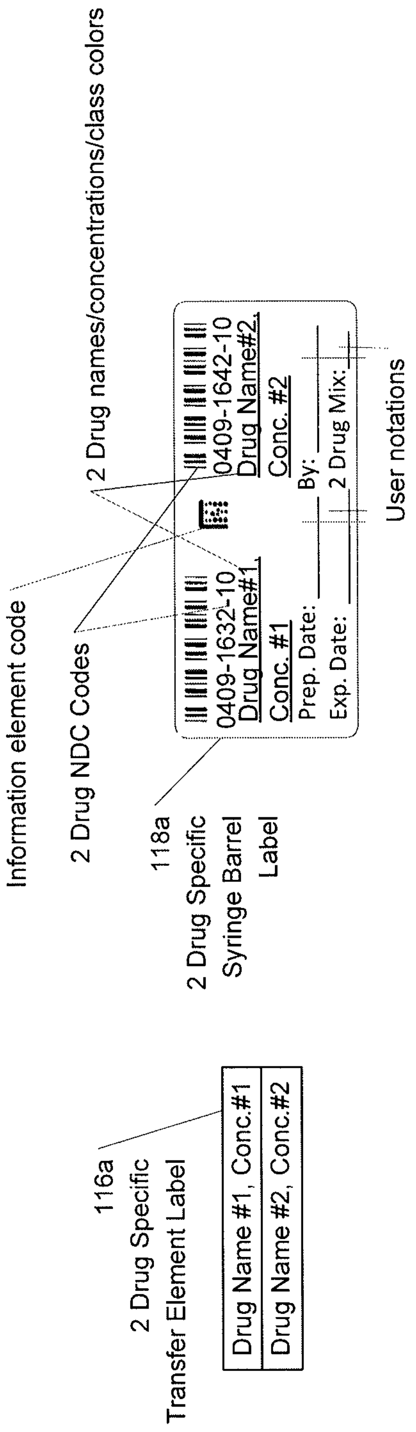
FIG. 31 describes alternate labeling for use with two medications.

FIG. 30 is a diagram illustrating a medication and identification information transfer system used with two primary medications. Some care providers prefer to mix medications in secondary containers. In this variation medication is provided in two vials (vial #1 and vial #2) and are sequentially withdrawn into the same secondary container 12. The mixed medication is injected into the patient. Examples of these types of medication mixes include: Propofol and Lidocaine, Neostigmine and Glycoprrolate, Meperidine and Promethazine, Bupivacaine and Epinepherine, among others. A variation of medication and identification information transfer system 2 can be used in this situation. As shown in FIG. 30, pharmacy package 94 can contain two vials of medication and one information transfer apparatus 10. As shown in FIG. 31, labels 116*a* and 118*a* can include information about two drugs (#1 and #2). The process for use is similar to FIG. 25, but now two medications can be withdrawn into one secondary container (syringe) 12, mixed and injected into the patient as a mix. The following steps are numbered in sequence and generally progress from left to right:

1. A dual drug vial pharmacy pack 94 is opened by the healthcare provider. Vial #1 and Vial #2 are removed from pack 94 and the caps flipped off.
2. Secondary container (syringe) 12 and information transfer apparatus 10 are removed from their packaging and syringe 12 is attached to information transfer apparatus 10.
3. Secondary label 118*a* (mixed medication label) is applied to syringe 12 identifying the mixed medication.
4. Vial #1 is punctured by vial adapter 6.
5. Syringe 12 and vial #1 are inverted and medication #1 is withdrawn from vial #1. Vial adapter 6 is removed from vial #1 (not shown).
6. Syringe 12 and vial adapter 6 along with medication #1 are spiked into vial #2.

7. Vial #2 and syringe 12 are inverted and medication #2 is withdrawn from vial #2 into syringe 12. This forms the mixed medication.
8. Syringe 12 and information element 8 are detached from vial adapter 6 and vial #2. The secondary container 12 with two medications can be shaken by the healthcare provider to ensure a good mix.
9. Syringe 12 and information element 8 are attached to intelligent injection site 110 for administration.
10. The medication is injected and data is transmitted to a data collection system (not shown). Note: The injection site can be part of a fluid delivery line from an IV source to the patient.

FIG. 31 describes alternate labeling for use with two medications as in

FIG. 30. Label 116*a* to the left can indicate that there are two medications and concentrations included. The background colors for each drug can be specific to the classification type. Similarly, label 118*a* can indicate that there are two drugs mixed together. The drug names, concentration, NDC number and associated barcode, classification color can be included to identify the mixed medication in secondary container 12. User notations can be included to designate the preparer, preparation date/time, expiration date/time, indication of a mixed solution, special handling instructions (protect from light, refrigerate, etc.).

The subject matter described herein can be embodied in systems, apparatus, methods, and/or articles depending on the desired configuration. In particular, aspects of the subject matter described herein can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications, applications, components, or code) include machine instructions for a programmable processor, and can be implemented in a high-level procedural and/or object-oriented programming language, and/or in assembly/machine language. As used herein, the term “machine-readable medium” refers to any non-transitory computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term “machine-readable signal” refers to any signal used to provide machine instructions and/or data to a programmable processor.

The implementations set forth in the foregoing description do not represent all implementations consistent with the subject matter described herein. Instead, they are merely some examples consistent with aspects related to the described subject matter. Wherever possible, the same reference numbers will be used throughout the drawings to refer to the same or like parts.

Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows and steps for use described herein do not require the particular order shown, or sequential order, to achieve desirable results. Other embodiments can be within the scope of the following claims.

What is claimed is:

1. A system comprising:

a primary medication container containing medication;

a secondary medication container; and an information transfer apparatus configured to enable the primary medication container to couple to the secondary medication container, the coupling allowing medication to flow from the primary medication container to the secondary medication container, wherein at least a portion of the information transfer apparatus automatically physically affixes and transfers from the primary medication container to the secondary medication container when the primary medication container decouples from the secondary medication container, the information transfer apparatus having an information transfer element to enable characterization of the medication;

wherein the information transfer element is automatically detected by at least one sensor of a medication injection site for manually administering the medication to a patient when the secondary medication container is being fluidically and rotatably coupled to the medication injection site.

2. A system as in claim 1, further comprising: a secondary medication container label characterizing the medication, the secondary medication container label being affixable to the secondary container.

3. A system as in claim 1, wherein the primary medication container is selected from a group consisting of: prefilled syringes, prefilled cartridges, vials, bottles, bags, and ampoules.

4. A system as in claim 1, wherein the information transfer element comprises both machine-readable identification information and human-readable identification information.

5. A system as in claim 1, wherein the information transfer apparatus comprises:

an information transfer element; and an adapter configured to couple to the information transfer element on a first end and to pierce and/or to couple to the primary medication container on a second end.

6. A system as in claim 5, wherein a fluid channel is formed through the information transfer element and the adapter from the primary medication container on a proximal end and the secondary medication container on a distal end.

7. A system as in claim 5, wherein the information transfer element further comprises:

a connector providing a releasable connection to the adapter allowing a user to readily disconnect the information transfer element from the adapter.

8. A system as in claim 5, wherein the information transfer element further comprises:

a connector providing a releasable connection to the secondary medication container preventing a user from readily disconnecting the information transfer element from the secondary medication container.

9. A system as in claim 8, wherein the connector comprises elastomeric material.

10. A system as in claim 5, wherein the information transfer apparatus comprises a housing, and wherein the information transfer element comprises an information element affixed to an outer surface of the housing.

11. A system as in claim 5, wherein the information transfer apparatus comprises a housing, and wherein the information transfer element comprises an information element encoded or deposited on an outer surface of the housing.

12. A system as in claim 5, wherein the information transfer apparatus comprises a housing, and wherein the information transfer element comprises an information element embedded within at least a portion of the housing.

13. A system as in claim 1 further comprising the medication injection site.

14. A system as in claim 1, wherein the medication injection site comprises:

a housing;

a fluid conduit at least partially extending within the housing and configured to deliver medication within a medication container to the patient;

a medication port extending from an external surface of the housing configured to be coupled to a fluid outlet of the medication container, the medication port being fluidically and directly coupled to the fluid conduit;

the at least one sensor, wherein the at least one sensor is disposed within the housing to generate data characterizing administration of the medication;

a transmitter within the housing to wirelessly transmit data generated by the sensor to a remote data collection system; and a self-contained power source within the housing powering the at least one sensor and the transmitter.

15. A system comprising:

a primary medication container containing medication;

a secondary medication container; and an information transfer apparatus configured to enable the primary medication container to couple to the secondary medication container, the coupling allowing medication to flow from the primary medication container to the secondary medication container, wherein at least a portion of the information transfer apparatus automatically physically affixes and transfers from the primary medication container to the secondary medication container when the primary medication container decouples from the secondary medication container;

wherein the information transfer apparatus comprises:

an adapter configured to couple to an information transfer element on a first end and to pierce and/or to couple to the primary medication container on a second end; and an information transfer element characterizing medicine contained within the primary medication container;

wherein the information transfer element is automatically detected by at least one sensor of a medication injection site for manually administering the medication to a patient when the secondary medication container is being fluidically and rotatably coupled to the medication injection site.

16. A system as in claim 15 further comprising the medication injection site.

17. A system as in claim 15, wherein the medication injection site comprises:

a housing;

a fluid conduit at least partially extending within the housing and configured to deliver medication within a medication container to the patient;

a medication port extending from an external surface of the first housing configured to be coupled to a fluid outlet of the medication container, the medication port being fluidically and directly coupled to the fluid conduit;

the at least one sensor, wherein the at least one sensor is disposed within the housing to generate data characterizing administration of the medication;

a transmitter within the housing to wirelessly transmit data generated by the sensor to a remote data collection system; and a self-contained power source within the housing powering the at least one sensor and the transmitter.

18. A system comprising:

a primary medication container containing medication;

a secondary medication container; and an information transfer apparatus configured to enable the primary medication container to couple to the secondary medication container, the coupling allowing medication to flow from the primary medication container to the secondary medication container, wherein at least a portion of the information transfer apparatus physically affixes or remains physically affixed to at least one of the (i) primary medication container and the (ii) secondary medication container when the primary medication container decouples from the secondary medication container, the information transfer apparatus having an information transfer element to enable characterization of the medication;

wherein:

the information transfer element is automatically detected by at least one sensor of a medication injection site for manually administering the medication to a patient; and the medication injection site comprises:

a housing;

a fluid conduit at least partially extending within the housing and configured to deliver medication within a medication container to the patient;

a medication port extending from an external surface of the housing configured to be coupled to a fluid outlet of the medication container, the medication port being fluidically and directly coupled to the fluid conduit;

the at least one sensor, wherein the at least one sensor is disposed within the housing to generate data characterizing administration of the medication;

a transmitter within the housing to wirelessly transmit data generated by the sensor to a remote data collection system; and a self-contained power source within the housing powering the at least one sensor and the transmitter.

19. A system comprising:

a primary medication container containing medication;

a secondary medication container; and an information transfer apparatus configured to enable the primary medication container to couple to the secondary medication container, the coupling allowing medication to flow from the primary medication container to the secondary medication container, wherein at least a portion of the information transfer apparatus physically affixes or remains physically affixed to at least one of the (i) primary medication container and the (ii) secondary medication container when the primary medication container decouples from the secondary medication container;

wherein the information transfer apparatus comprises:

an adapter configured to couple to an information transfer element on a first end and to pierce and/or to couple to the primary medication container on a second end; and an information transfer element characterizing medicine contained within the primary medication container;

wherein:

the information transfer element is automatically detected by at least one sensor of a medication injection site for manually administering the medication to a patient; and the medication injection site comprises:

a housing;

a fluid conduit at least partially extending within the housing and configured to deliver medication within a medication container to the patient;

a medication port extending from an external surface of the housing configured to be coupled to a fluid outlet of the medication container, the medication port being fluidically and directly coupled to the fluid conduit;

the at least one sensor, wherein the at least one sensor is disposed within the housing to generate data characterizing administration of the medication;

a transmitter within the housing to wirelessly transmit data generated by the sensor to a remote data collection system; and a self-contained power source within the housing powering the at least one sensor and the transmitter.

* * * * *